(12) United States Patent
Vanderzande et al.

(10) Patent No.: US 8,329,923 B2
(45) Date of Patent: Dec. 11, 2012

(54) 4, 4' DISUBSTITUTED 4H-CYCLOPENTADITHIOPHENE AND NEW METHODS FOR SYNTHESIZING THE SAME

(75) Inventors: Dirk Vanderzande, Hasselt (BE); Laurence Lutsen, Coudekerque-Branche (FR); Sarah Van Mierloo, Diepenbeek (BE)

(73) Assignees: IMEC, Leuven (BE); Universiteit Hasselt, Diepenbeek (BE)

( * ) Notice: Subject to any disclaimer, the term of this patent is extended or adjusted under 35 U.S.C. 154(b) by 196 days.

(21) Appl. No.: 13/028,539

(22) Filed: Feb. 16, 2011

(65) Prior Publication Data
US 2011/0313175 A1 Dec. 22, 2011

Related U.S. Application Data

(60) Provisional application No. 61/356,005, filed on Jun. 17, 2010.

(30) Foreign Application Priority Data

Jun. 17, 2010 (EP) .................................... 10166282

(51) Int. Cl.
*C07D 409/14* (2006.01)
(52) U.S. Cl. ......................................... 549/4
(58) Field of Classification Search ........ 549/4
See application file for complete search history.

(56) References Cited

OTHER PUBLICATIONS

Brzezinski et al., Synthesis, 2002, 8, 1053-1056.
Coppo et al., Macromolecules, 2003, 36, 2705-2711.
Wang et al. J. Am. Chem. Soc., 2008, 130, 5392-5393.
Zotti et al., Macromolecules, 2001, 34, 3889-3895.

*Primary Examiner* — Taofiq A Solola
(74) *Attorney, Agent, or Firm* — Knobbe Martens Olson & Bear, LLP

(57) ABSTRACT

The present preferred embodiments relate to a method for the synthesis of a compound having the following general formula:

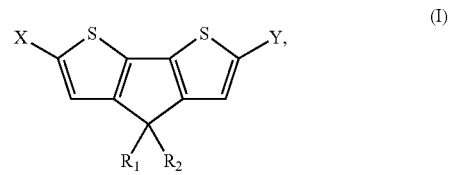

the method comprising the step of reacting, in presence of a diprotic acid having a negative pKa, a compound having the general formula:

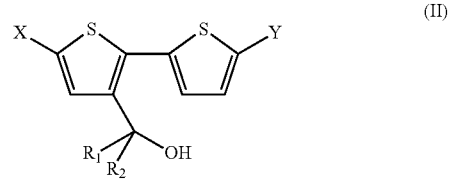

wherein $R_1$ and $R_2$ are organic groups and wherein X and Y are independently selected from the group consisting of hydrogen, chloro, bromo, iodo, boronic acid, boronate esters, borane, pseudohalogen and organotin. It further relates to compounds so obtained and to compounds resulting from the ring closure of compound (II).

11 Claims, No Drawings

4,4' DISUBSTITUTED 4H-CYCLOPENTADITHIOPHENE AND NEW METHODS FOR SYNTHESIZING THE SAME

CROSS-REFERENCE TO RELATED APPLICATIONS

This application claims the benefit under 35 U.S.C. §119 (e) of U.S. provisional application Ser. No. 61/356,005, filed Jun. 17, 2010, and claims the benefit under 35 U.S.C. §119 (a)-(d) of European application No. 10166282.3, filed Jun. 17, 2010, the disclosures of which are hereby expressly incorporated by reference in their entirety and are hereby expressly made a portion of this application.

TECHNICAL FIELD OF THE PREFERRED EMBODIMENTS

The present preferred embodiments relate to a synthetic method for obtaining 4,4' disubstituted 4H-cyclopentadithiophene, to new 4,4' disubstituted 4H-cyclopentadithiophene.

BACKGROUND OF THE PREFERRED EMBODIMENTS

The preparation and purification of 4,4-bis(alkyl)-4H-cyclopenta[2,1-b:3,4-b:]dithiophenes has recently attracted much attention as such molecules are useful building blocks in e.g. organic electronics.

Brzezinski et al. (Synthesis 2002, 8, 1053-1056) have proposed a three-step approach to 4H-cyclopenta[2,1-b:3,4-b']dithiophen-4-one.

Coppo et al. (Macromolecules, 2003, 36, 2705-2711) reduced 4H-cyclopenta[2,1-b:3,4-b']dithiophen-4-one with hydrazine according to a Huang-Minlon modification of the Wolf-Kischner procedure, thereby obtaining 4H-cyclopentadithiophene. They then performed a dialkylation with alkyl halogenides under basic conditions resulting in 4,4-bis(alkyl)-4H-cyclopenta[2,1-b:3,4-b']dithiophenes.

Zotti et al. (macromolecule, 2001, 34, 3889-3895) synthesized 4,4' asymmetrically disubstituted 4H-cyclopentadithiophene by performing two separate alkylation steps on 4H-cyclopentadithiophene with two different alkyl halogenides under basic conditions.

This overall procedure toward 4,4-$R_1R_2$-4H-cyclopenta[2,1-b:3,4-b']dithiophenes wherein $R_1$ is different from $R_2$ requires 6 synthesis steps and requires the difficult separation of mono and disubstituted 4H-cyclopentadithiophene. Also, the presence of mono-substituted 4H-cyclopentadithiophene as an impurity, even in small amounts, is likely detrimental to it use in optoelectronic applications because the hydrogen at the 4 position is foreseen as being easily oxidized. Furthermore this 6 steps synthesis involves the use of the highly toxic hydrazine.

There is therefore a need in art for a new synthetic route toward 4,4' disubstituted 4H-cyclopentadithiophene and especially asymmetrically disubstituted 4H-cyclopentadithiophene.

SUMMARY OF THE PREFERRED EMBODIMENTS

It is an object of the present preferred embodiments to provide alternative methods for the synthesis of 4,4' disubstituted 4H-cyclopentadithiophene and especially asymmetrically disubstituted 4H-cyclopentadithiophene.

It is an advantage of embodiments of the present preferred embodiments that the methods are very versatile and allow the incorporation of a large variety of substituents at the 4-position of the 4H-cyclopentadithiophene.

It is a further advantage of embodiments of the present preferred embodiments that they do not require the use of the highly toxic compound hydrazine.

It is a further advantage of embodiments of the present preferred embodiments that the method proceeds in a reduced number of steps. The synthesis can proceed in three steps if a commercially available ketone is used.

It is a further advantage of embodiments of the present preferred embodiments that no monosubstituted 4H-cyclopentadithiophene is present as an impurity in the disubstituted 4H-cyclopentadithiophene as produced.

In a first aspect, the present preferred embodiments relates to a method for the synthesis of a compound having the following general formula:

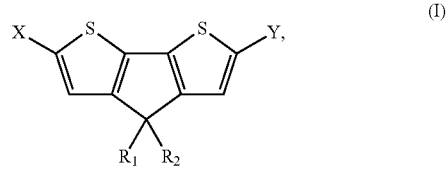

(I)

the method comprising the step of contacting a compound having the general formula:

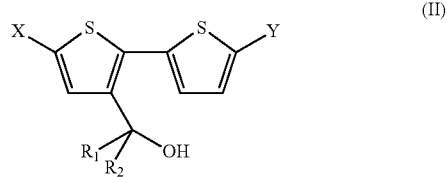

(II)

with a diprotic acid having a negative pKa, wherein $R_1$ and $R_2$ are organic groups and wherein X and Y are independently selected from the group consisting of hydrogen, chloro, bromo, iodo, boronic acid, boronate esters, borane, pseudohalogen and organotin. The case where X=Y=H is preferred.

In a second aspect, the present preferred embodiments relates to a chemical compound having the general formula:

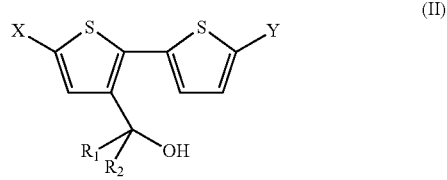

(II)

wherein $R_1$ and $R_2$ are independently selected from the group consisting of $C_{1-20}$ alkyl, halo $C_{1-20}$ alkyl, $C_{4-10}$ cycloalkyl, $C_{1-3}$ alkyl $C_{1-10}$ alkanoate, $C_{1-3}$ alkyl $C_{1-10}$ alkanamide, $C_{2-10}$ alkenyl, $C_{3-10}$ cycloalkenyl, aryl $C_{1-5}$ alkyl, di-aryl $C_{1-5}$ alkyl, tri-$C_{1-20}$ aryl $C_{1-5}$ alkyl, aryl $C_{2-5}$ alkenyl, $C_{2-10}$ alkynyl, $C_{1-10}$ alkanol, $C_{1-10}$ alkanethiol, aryl, heterocyclic radicals (e.g. heteroaryl), $C_{1-3}$ alkoxy $C_{1-3}$ alkyl, di-$C_{1-3}$ alkoxy $C_{1-3}$ alkyl, $C_{1-3}$ alkyloxy aryl $C_{1-3}$ alkyl, $C_{1-3}$ alkyl aryl, $C_{1-3}$ alkyl sulfanyl $C_{1-3}$ alkyl, $C_{1-3}$ alkyl aryl sulfanyl $C_{1-3}$ alkyl, aryloxy $C_{1-3}$ alkyl, N,N—$C_{1-3}$ dialkyl $C_{1-3}$ alkylamine, N—$C_{1-3}$ alkyl $C_{1-3}$ alkylamine, aryl sulphonyl $C_{1-3}$ alkyl or $R_1$ and $R_2$ form together a cycloalkyl group or a heterocyclic group, and wherein X and Y are independently selected from the group consisting of hydrogen, chloro, bromo, iodo, boronic acid, boronate esters, borane, pseudohalogen and organotin. The case where X=Y=H is preferred.

In a third aspect, the present preferred embodiments relates to a chemical compound having the general formula

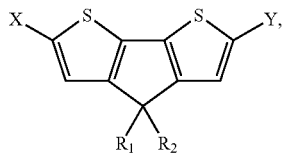

wherein $R_1$ and $R_2$ are independently selected from the group consisting of $C_{1-20}$ alkyl, halo $C_{1-20}$ alkyl, $C_{4-10}$ cycloalkyl, $C_{1-3}$ alkyl $C_{1-10}$ alkanoate, $C_{1-3}$ alkyl $C_{1-10}$ alkanamide, $C_{2-10}$ alkenyl, $C_{3-10}$ cycloalkenyl, aryl $C_{1-5}$ alkyl, di-aryl $C_{1-5}$ alkyl, tri-$C_{1-20}$ aryl $C_{1-5}$ alkyl, aryl $C_{2-5}$ alkenyl, $C_{2-10}$ alkynyl, $C_{1-10}$ alkanol, $C_{1-10}$ alkanethiol, aryl, heterocyclic radicals (e.g. heteroaryl), $C_{1-3}$ alkoxy $C_{1-3}$ alkyl, di-$C_{1-3}$ alkoxy $C_{1-3}$ alkyl, $C_{1-3}$ alkyloxy aryl $C_{1-3}$ alkyl, $C_{1-3}$ alkyl aryl, $C_{1-3}$ alkyl sulfanyl $C_{1-3}$ alkyl, $C_{1-3}$ alkyl aryl sulfanyl $C_{1-3}$ alkyl, aryloxy $C_{1-3}$ alkyl, N,N—$C_{1-3}$ dialkyl $C_{1-3}$ alkylamine, N—$C_{1-3}$ alkyl $C_{1-3}$ alkylamine, aryl sulphonyl $C_{1-3}$ alkyl or $R_1$ and $R_2$ form together a cycloalkyl group or a heterocyclic group and wherein X and Y are independently selected from the group consisting of hydrogen, chloro, bromo, iodo, boronic acid, boronate esters, borane, pseudohalogen and organotin.

The above objective is accomplished by methods according to the present preferred embodiments.

Particular and preferred aspects of the preferred embodiments are set out in the accompanying independent and dependent claims. Features from the dependent claims may be combined with features of the independent claims and with features of other dependent claims as appropriate and not merely as explicitly set out in the claims.

The above and other characteristics, features and advantages of the present preferred embodiments will become apparent from the following detailed description which illustrates, by way of example, the principles of the preferred embodiments. This description is given for the sake of example only, without limiting the scope of the preferred embodiments.

DESCRIPTION OF ILLUSTRATIVE EMBODIMENTS

The present preferred embodiments will be described with respect to particular embodiments but the preferred embodiments is not limited thereto but only by the claims.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the preferred embodiments described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the preferred embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present preferred embodiments, the only relevant components of the device are A and B.

Reference throughout this specification to "one embodiment" or "an embodiment" means that a particular feature, structure or characteristic described in connection with the embodiment is included in at least one embodiment of the present preferred embodiments. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the preferred embodiments, various features of the preferred embodiments are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed preferred embodiments requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this preferred embodiment.

Furthermore, while some embodiments described herein include some but not other features included in other embodiments, combinations of features of different embodiments are meant to be within the scope of the preferred embodiments, and form different embodiments, as would be understood by those in the art. For example, in the following claims, any of the claimed embodiments can be used in any combination.

In the description provided herein, numerous specific details are set forth. However, it is understood that embodiments of the preferred embodiments may be practiced without these specific details. In other instances, well-known methods, structures and techniques have not been shown in detail in order not to obscure an understanding of this description.

The following definitions of terms are provided solely to assist in the understanding of the preferred embodiments.

As used herein, with respect to a substituting radical, and unless otherwise stated, the term "$C_{1-n}$ alkyl" refers to a straight or branched chain saturated acyclic hydrocarbon radical having from 1 to n carbon atoms such as, for example, methyl, ethyl, propyl, n-butyl, 1-methylethyl(isopropyl), 2-methylpropyl(isobutyl), 1,1-dimethylethyl(ter-butyl), pentyl, hexyl, heptyl, octyl, nonyl, decyl and dodecyl amongst others.

As used herein, with respect to a substituting radical, and unless otherwise stated, the term "halo $C_{1-n}$ alkyl" means a $C_{1-n}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl, chloromethyl and the like.

As used herein, with respect to a substituting radical, and unless otherwise stated, the term "$C_{1-m}$ alkyl $C_{1-n}$ alkanoate" refers to an ester group having from 1 to m carbon atoms in the chain attached to the "ether" oxygen and having from 1 to n carbon atoms in the chain comprising the carboxyl group.

As used herein, with respect to a substituting radical, and unless otherwise stated, the term "$C_{2-n}$ alkenyl" designate a straight or branched acyclic hydrocarbon monovalent radical having one or more ethylenic unsaturations and having from 2 to n carbon atoms such as, for example, vinyl, 1-propenyl, 2-propenyl(allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein, with respect to a substituting radical, and unless otherwise stated, the term "$C_{2-n}$ alkynyl" defines straight and branched chain hydrocarbon monovalent radicals containing one or more triple bonds and optionally at least one double bond and having from 2 to n carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein, with respect to a substituting radical, and unless otherwise stated, the term "cycloalkyl" means a mono- or polycyclic saturated hydrocarbon monovalent radical having from 4 to 10 carbon atoms, such as for instance cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl and the like, wherein each carbon atom of the cycloalkyl may furthermore be independently substituted with a substituent selected from the group consisting of halogen, nitro, $C_{1-7}$ alkyl (optionally containing one or more functions or radicals selected from the group consisting of carbonyl(oxo), alcohol(hydroxyl), ether(alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof.

As used herein with respect to a substituting radical, and unless otherwise stated, the term "acyl" broadly refers to a substituent derived from an acid such as an organic monocarboxylic acid, a carbonic acid, a carbamic acid (resulting in a carbamoyl substituent) or the thioacid or imidic acid (resulting in a carbamidoyl substituent) corresponding to the acids. A more specific kind of "acyl" group within the scope of the above definition refers to a carbonyl(oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl groups originating from aliphatic or cycloaliphatic monocarboxylic acids are designated herein as aliphatic or cycloaliphatic acyl groups and include, but are not limited to, the following:

alkanoyl (for example formyl, acetyl, propionyl, butyryl, isobutyryl, valeryl, isovaleryl, pivaloyl and the like);

cycloalkanoyl (for example cyclobutanecarbonyl, cyclopentanecarbonyl, cyclo-hexanecarbonyl, 1-adamantanecarbonyl and the like);

cycloalkyl-alkanoyl (for example cyclohexylacetyl, cyclopentylacetyl and the like);

alkenoyl (for example acryloyl, methacryloyl, crotonoyl and the like);

alkylthioalkanoyl (for example methylthioacetyl, ethylthioacetyl and the like);

alkoxycarbonyl (for example methoxycarbonyl, ethoxycarbonyl, propoxycarbonyl, isopropoxycarbonyl, butoxycarbonyl, isobutoxycarbonyl and the like);

alkylcarbamoyl (for example methylcarbamoyl and the like);

(N-alkyl)-thiocarbamoyl (for example (N-methyl)-thiocarbamoyl and the like);

alkylcarbamidoyl (for example methylcarbamidoyl and the like); and alkoxyalkyl (for example methoxyalkyl, ethoxyalkyl, propoxyalkyl and the like);

Acyl groups may also originate from aromatic monocarboxylic acids and include, but are not limited to, the following:

aroyl (for example benzoyl, toluoyl, xyloyl, 1-naphthoyl, 2-naphthoyl and the like);

arylalkanoyl (for example phenylacetyl and the like);

arylalkenoyl (for example cinnamoyl and the like);

aryloxyalkanoyl (for example phenoxyacetyl and the like);

arylthioalkanoyl (for example phenylthioacetyl and the like);

arylaminoalkanoyl (for example N-phenylglycyl, and the like);

aryloxycarbonyl (for example phenoxycarbonyl, naphthyloxycarbonyl and the like);

arylalkoxycarbonyl (for example benzyloxycarbonyl and the like);

arylcarbamoyl (for example phenylcarbamoyl, naphthylcarbamoyl and the like);

arylglyoxyloyl (for example phenylglyoxyloyl and the like).

arylthiocarbamoyl (for example phenylthiocarbamoyl and the like); and arylcarbamidoyl (for example phenylcarbamidoyl and the like).

Acyl groups may also originate from heterocyclic monocarboxylic acids and include, but are not limited to, the following:

heterocyclic-carbonyl, in which the heterocyclic group is as defined herein, preferably an aromatic or non-aromatic 5- to 7-membered heterocyclic ring with one or more heteroatoms selected from the group consisting of nitrogen, oxygen and sulfur in the ring (for example thiophenoyl, furoyl, pyrrolecarbonyl, nicotinoyl and the like); and heterocyclic-alkanoyl in which the heterocyclic group is as defined herein, preferably an aromatic or non-aromatic 5- to 7-membered heterocyclic ring with one or more heteroatoms selected from the group consisting of nitrogen, oxygen and sulfur in the ring (for example thiophenylacetyl, furylacetyl, imidazolylpropionyl, tetrazolylacetyl, 2-(2-amino-4-thiazolyl)-2-methoxyiminoacetyl and the like).

As used herein with respect to a substituting radical (for instance formed by $R_1$ and $R_2$ together), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of the rings having from 3 to 10 atoms (and optionally further including one or more heteroatoms attached to one or more carbon atoms of the ring, for instance in the form of a carbonyl or thiocarbonyl or selenocarbonyl group, and/or to one or more heteroatoms of the ring, for instance in the form of a sulfone, sulfoxide, N-oxide, phosphate, phosphonate or selenium oxide group), each of the heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphtho-triazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazolyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl(benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of the heterocyclic radical may furthermore be independently substituted with a substituent selected from the group consisting of halogen, nitro, $C_{1-7}$ alkyl (optionally containing one or more functions or radicals selected from the group consisting of carbonyl(oxo), alcohol(hydroxyl), ether(alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of the non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein and unless otherwise stated, the term "aryl" designate any mono- or polycyclic aromatic hydrocarbon radical having from 6 up to 30 carbon atoms such as but not limited to phenyl, naphthyl, anthracenyl, phenanthracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals such as, for instance, indanyl, tetrahydronaphthyl, fluorenyl, indenofluorenyl and the like, all of the radicals being optionally substituted with one or more substituents independently selected from the group consisting of halogen, amino (optionally substituted with one or two alkyl or aryl radicals), trifluoromethyl, hydroxyl, sulfhydryl, alkyl, aryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical and unless provided otherwise, the term arylene refers to a divalent aryl group.

As used herein with respect to a substituting radical and unless otherwise stated, the terms "arylalkyl" (e.g. $C_{5-6}$ aryl $C_{1-5}$ alkyl) and "arylalkenyl" (e.g. $C_{5-6}$ aryl $C_{2-5}$ alkenyl) refer to respectively an aliphatic saturated or ethylenically unsaturated hydrocarbon monovalent radical (respectively a $C_{1-n}$ alkyl and $C_{2-n}$ alkenyl radical such as defined above) onto which an aryl radical (such as defined above) is bonded via a carbon atom, and wherein the aliphatic radical and/or the aryl radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxyphenyl]ethyl, styryl and the likes.

As used herein with respect to a substituting radical and unless otherwise stated, the terms "di-arylalkyl" (e.g. di-$C_{5-6}$ aryl $C_{1-5}$ alkyl) and "tri-arylalkyl" (e.g. tri-$C_{5-6}$ aryl $C_{1-5}$ alkyl) refer to an aliphatic saturated hydrocarbon monovalent radical onto which respectively one or two aryl radicals (such as defined above) are bonded via a carbon atom, and wherein the aliphatic radical and/or the aryl radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to diphenylmethyl, triphenylmethyl and the likes.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methyl-benzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "$C_{1-n}$ alkanol", refer to a substituent wherein a carbon atom of a $C_{1-n}$ alkyl as defined above is attached to a hydroxyl group.

As used herein with respect to a substituting radical, and unless otherwise stated, the term "$C_{1-n}$ alkanethiol", refer to a substituent wherein a carbon atom of a $C_{1-n}$ alkyl as defined above is attached to a thiol group.

As used herein with respect to a substituting radical, and unless otherwise stated, the terms "$C_{1-n}$ alkyl sulfanyl $C_{1-m}$ alkyl" refers to a an alkyl radical having from 1 to m carbon atoms onto which a sulfur(thioether) atom is bonded, the sulfur atom being further bonded to a second alkyl group having 1 to m carbon atoms.

As used herein with respect to a substituting radical, and unless otherwise stated, the terms "$C_{1-n}$ alkyl aryl sulfanyl $C_{1-m}$ alkyl" refers to a an alkyl radical having from 1 to m carbon atoms onto which a sulfur (thioether) atom is bonded, the sulfur atom being further bonded to an aryl group, itself bounded to a second alkyl group having 1 to m carbon atoms.

As used herein with respect to a substituting radical, and unless otherwise stated, the terms "$C_{1-7}$ alkoxy", "$C_{3-10}$ cycloalkoxy", "aryloxy", "arylalkoxy", "oxyheterocyclic", "heterocyclic-substituted alkoxy", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl, heterocyclic radical or heterocyclic-substituted alkyl (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl and cresoxy, and various isomers of piperidinoxy, 1-methylpiperidinoxy, pyrrolidinoxy, pyridinoxy, tetrahydrofuranyloxy, morpholinoethoxy, piperazinoethoxy, piperi-dinoethoxy, pyridinoethoxy, pyrrolidinoethoxy, piperidinomethoxy, methylpyridinoxy, methylquinolinoxy, pyridinopropoxy and the like.

As used herein with respect to a substituting radical, and unless provided otherwise, the terms "alkoxyalkyl" and "dialkoxyalkyl" refer to an alkyl radical onto which respectively one and two alkoxy radical are bounded.

As used herein with respect to a substituting radical, and unless provided otherwise, the terms "aryloxyalkyl" refers to an alkyl radical onto which an oxygen ether atom is bounded, the atom being further bounded to an alkyl radical.

As used herein and unless provided otherwise, the term "alkoxyarylalkyl" relates to a an aliphatic saturated hydrocarbon monovalent radical (a $C_{1-n}$ alkyl radical such as defined above) onto which an aryl radical (such as defined above) is bounded via a carbon atom of the aryl radical, and wherein the aryl radical is further bounded to a $C_{1-7}$ alkoxy radical.

As used herein with respect to a substituting radical and unless provided otherwise, the term "N,N-dialkyl alkylamine" refers to a monovalent radical having an alkyl radical linked via a single bound to an amino atom, itself linked to two further alkyl groups.

As used herein with respect to a substituting radical and unless provided otherwise, the term "N-alkyl alkylamine" refers to a monovalent radical having an alkyl radical linked via a single bound to an amino atom, itself linked to a further alkyl group.

As used herein with respect to a substituting radical and unless provided otherwise, the term "aryl sulphonyl alkyl" relates to a monovalent radical having an alkyl radical linked by a single bond to the sulfur atom of a sulfone group, the sulfur atom being further linked to an aryl group.

As used herein with respect to a substituting radical and unless provided otherwise, the term "$C_{1-m}$ alkoxy $C_{1-n}$ alkyl" relates to a monovalent alkyl radical having 1 to n carbon atoms linked by a single bond to an ether oxygen, itself linked to a second alkyl chain having 1 to m carbon atoms.

As used herein with respect to a substituting radical, and unless otherwise stated, the term "organotin" refers to a group represented by the structural formula $SnR_9R_{10}R_{11}$ wherein each of $R_9$, $R_{10}$ and $R_{11}$ is independently selected from the group consisting of halogen, $C_{1-20}$ alkyl, $C_{3-10}$ cycloalkyl, aryl, benzyl and $C_{2-7}$ alkenyl, provided that $R_9$, $R_{10}$ and $R_{11}$ are not simultaneously halogen; such organotin groups may be derived from tin compounds including, but not limited to, di-n-butyltin dibromide, di-n-butyltin dichloride, di-tert-butyltin dichloride, dimethyltin dibromide, dimethyltin dichloride, dimethyltin difluoride, dimethyltin diiodide, diphenyltin dichloride, diphenyltin dibromide, diphenyltin difluoride, diphenyltin diiodide, tributyltin fluoride, tributyltin chloride, tributyltin bromide, tributyltin iodide, phenyltin tribromide, phenyltin trichloride, tricyclohexyltin chloride, triethyltin bromide, triethyltin chloride, triethyltin iodide, vinyltributyltin, tetrabutyltin, butyltin trichloride, n-butylvinyltin dichloride, diallyldibutyltin, diallyldiphenyltin, dibutylvinyltin bromide, dibutylvinyltin chloride, dichlorodi-m-tolylstannane, diethyldiisoamyltin, diethyldiisobutyltin, diethyldiphenyltin, diethylisoamyltin bromide, diethylisoamyltin chloride, diethylisobutyltin bromide, diethyl-n-propyltin bromide, diethyl-n-propyltin chloride, diethyl-n-propyltin fluoride, diethyltin dibromide, diethyltin dichloride, diethyltin difluoride, diethyltin diiodide, diisoamyltin dibromide, diisoamyltin dichloride, diisoamyltin diiodide, diisobutyltin dichloride, diisobutyltin diiodide, diisopropyltin dichloride, diisopropyltin dibromide, dimethyldiethyltin, dimethyldiisobutyltin, dimethyldioctyltin, dimethyldivinyltin, dimethylethylpropyltin, dimethylethyltin iodide, dimethyldivinyltin, dimethylvinyltin bromide, dimethylvinyltin iodide, diphenyldivinyltin, dipropyltin difluoride, dipropyltin diiodide, dipropyltin dichloride, dipropyltin dibromide, di-o-tolyltin dichloride, di-p-tolyltin dichloride, ditriphenyl-stannylmethane, divinylbutyltin chloride, divinyltin dichloride, ethyldiisoamyltin bromide, ethyldiisobutyltin bromide, ethylmethylpropyltin iodide, ethyl-n-propyldiisoamyltin, ethylpropyltin dichloride, ethyltin tribromide, ethyltin triiodide, ethyltri-n-butyltin, ethyltri-n-propyltin, methyltin tribromide, methyltin trichloride, methyltin triiodide, methyltri-n-butyltin, methyltri-n-propyltin, phenylbenzyltin dichloride, phenyltribenzyltin, propyltin triiodide, propyltri-n-amyltin, tetra-n-amyltin, tetra-n-butyltin, tetrabenzyltin, tetracyclohexyltin, tetraethyltin, tetra-n-heptyltin, tetra-n-hexyltin, tetraisoamyltin, tetraisobutyltin, tetralauryltin, tetramethyltin, tetra-n-octyltin, tetraphenyltin, tetrapropyltin, tetra-o-tolyltin, tetra-m-tolyltin, tetra-p-tolyltin, tetravinyltin, tetra-m-xylyltin, tetra-p-xylyltin, o-tolyltin trichloride, p-tolyltin trichloride, m-tolyltrichlorostannane, triallylbutyltin, tri-n-amyltin bromide, tribenzylethyltin, tribenzyltin chloride, tribenzyltin iodide, tri-n-butyltin bromide, tri-n-butylvinyltin, triethyl-n-amyltin, triethylisoamyltin, triethylisobutyltin, triethylphenyltin, triethyl-n-propyltin, triisoamyltin bromide, triisoamyltin chloride, triisoamyltin fluoride, triisoamyltin iodide, triisobutylethyltin, triisobutylisoamyltin, triisobutyltin bromide, triisobutyltin chloride, triisobutyltin fluoride, triisobutyltin iodide, triisopropyltin bromide, triisopropyltin iodide, trimethyldecyltin, trimethyldodecyltin, trimethylethyltin, trimethyltin bromide, trimethyltin chloride, trimethyltin fluoride, trimethyltin iodide, triphenylallyltin, triphenylbenzyltin, triphenylbutyltin, triphenylethyltin, triphenylmethyltin, triphenyl-α-naphthyltin, triphenyltin bromide, triphenyltin chloride, triphenyltin fluoride, triphenyltin iodide, triphenyl-p-tolyltin, triphenyl-p-xylyltin, tri-n-propyl-n-butyltin, tri-n-propylethyltin, tri-n-propylisobutyl tin, tri-n-propyltin chloride, tri-n-propyltin fluoride, tri-n-propyltin iodide, tri-o-tolyltin bromide, tri-p-tolyltin bromide, tri-o-tolyltin chloride, tri-m-tolyltin chloride, tri-p-tolyltin chloride, tri-p-tolyltin fluoride, tri-o-tolyltin iodide, tri-p-tolyltin iodide, triphenylstannylmethane, trivinyldecyltin, trivinylhexyltin, trivinyloctyltin, trivinyltin chloride, vinyltin trichloride, tri-p-xylyltin bromide, tri-p-xylyltin chloride, tri-p-xylyltin fluoride, tri-p-xylyltin iodide and tri-m-xylyltin fluoride.

As used herein with respect to a substituting radical, and unless otherwise stated, the term "boronate ester" refers to a boronic acid derivative wherein hydrogen is replaced by any organic residue, preferably a hydrocarbyl group, and which can be obtained by condensation with alcohols or diols, including but not limited to dioxaborolanes and dioxaborinanes.

As used herein with respect to a substituting radical and unless provided otherwise, the term "pseudo-halogen" refers to a chemical group that behaves like a halogen in reductive coupling reactions. For instance it can be selected from the group consisting of trifluoromethylphenylmethanesulfonyl, para-toluenesulfonyl, triflate and methanesulfonyl.

The preferred embodiments will now be described by a detailed description of several embodiments of the preferred embodiments.

In a first aspect, the present preferred embodiments relates to a method for the synthesis of a compound having the following general formula (I):

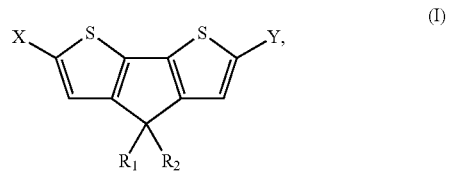

the method comprising the step of contacting a compound having the general formula (II):

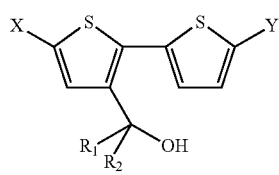

(II)

with a diprotic acid having a negative pKa, wherein $R_1$ and $R_2$ are independently selected among organic groups and wherein X and Y are independently selected from the group consisting of hydrogen, chloro, bromo, iodo, boronic acid, boronate esters, borane, pseudohalogen and organotin. The case where X=Y=H is preferred.

In embodiments, $R_1$ and $R_2$ may be independently selected from the group consisting of organic groups comprising one or more chains and/or rings of atoms, comprising from 1 to 65 carbon atoms and preferably from 1 to 30 carbon atoms and optionally from 1 to 25 halogen atoms and/or from 1 to 6 oxygen atoms and/or from 1 to 2 sulfur atoms and/or from 1 to 2 nitrogen atoms.

In embodiments, the organic groups may comprise from 1 to 30 carbon atoms, preferably from 1 to 25 carbon atoms and more preferably from 1 to 21 carbon atoms, even more preferably from 1 to 15 carbon atoms, even more preferably from 1 to 12 carbon atoms. The organic groups can optionally comprise one or more linear or branched chains of atoms comprising carbon atoms (e.g. alkyl chains). The organic groups can optionally comprise one or more rings comprising carbon atoms (e.g. aryl groups). A chain of atoms interrupted by a ring is considered as consisting in two chains of atoms and one ring. Each of the rings can comprise from 4 to 7 atoms and preferably from 4 to 6 atoms. Each of the rings can comprise from 3 to 6 carbon atoms. Each ring can comprise one or two heteroatoms such as nitrogen, sulfur or oxygen. The rings can be aromatic or not. The organic groups (e.g. chains or rings) can optionally comprise one or more unsaturations such as double or triple bounds (e.g. alkene, alkyne or aryl groups comprising carbon atoms). The number of unsaturation is the group can for instance be from 1 to 10. When two or more rings are presents they can form fused rings.

In embodiments, the organic groups may comprise both chains and rings separated or not by a heteroatom such as sulfur, oxygen or nitrogen.

In addition to the carbon atoms, the organic groups can comprise other atoms as described in the embodiments below.

In embodiments, the organic groups may be halogenated. The halogen atom(s) may for instance substitute a carbon chain such as an alkyl chain or may substitute a ring such as an aromatic ring. For instance the organic groups may be perhalogenated (e.g. perfluorinated). In such embodiments, the number of halogen atoms in the organic group can be fairly high, for instance from 3 to 25.

In embodiments, the organic groups optionally comprises from 1 to 25 halogens, preferably from 1 to 6 halogens, preferably from 1 to 3 halogens. The halogens can be all the same or can be each selected independently from one another. The halogens are preferably selected from Br, Cl, I and F. Preferably, they are selected from F, Br and Cl.

In embodiments, the organic groups optionally comprise one, two or three chlorine atoms.

In embodiments, the organic groups optionally comprise one, two or three Bromine atoms.

In embodiments, the organic groups optionally comprise one, two, three, four, five or six Fluorine atoms.

In embodiments, the organic groups optionally comprise from 1 to 6 oxygen atoms (e.g. in oligoethyleneglycol chains), preferably from 1 to 3 oxygen atoms. The oxygen atom can for instance belong to an alcohol or alcoholate group, to an ether or to a sulfone group. The oxygen atom(s) may for instance be linked to a carbon chain such as an alkyl chain or may substitute a ring such as an aromatic ring or may be part of a ring such as in a furane group. The oxygen atoms may be part of an ester group, a thioester group or a thionoester group.

In embodiments, the organic groups optionally comprise one, two, three, four, five or six oxygen atoms.

In embodiments, the organic groups optionally comprise from 1 to 2 sulfur atoms. The sulfur atom can for instance belong to a thiol or thiolate group, to a thioether or a sulfone group. The sulfur atom(s) may for instance be linked to a carbon chain such as an alkyl chain or may substitute a ring such as an aromatic ring or may be part of a ring such as in a thiophene group. The sulfur atom can for instance belong to a thioester group, a thionoester group or a disulphide group.

In embodiments, the organic groups optionally comprise from 1 to 2 nitrogen atoms. The nitrogen atom can for instance be incorporated in the form of a primary, a secondary or a tertiary amino group. The nitrogen atom(s) may for instance be linked to a carbon chain such as an alkyl chain. The nitrogen atom can for instance be part of a saturated or unsaturated (e.g. aromatic) ring such as in a pyridine group.

Preferably, $R_1$ and $R_2$ are independently selected from the group consisting of $C_{1-20}$ alkyl, halo $C_{1-20}$ alkyl, $C_{4-10}$ cycloalkyl, $C_{1-3}$ alkyl $C_{1-10}$ alkanoate, $C_{1-3}$ alkyl $C_{1-10}$ alkanamide, $C_{2-10}$ alkenyl, $C_{3-10}$ cycloalkenyl, aryl $C_{1-5}$ alkyl, di-aryl $C_{1-5}$ alkyl, tri-$C_{1-20}$ aryl $C_{1-5}$ alkyl, aryl $C_{2-5}$ alkenyl, $C_{2-10}$ alkynyl, $C_{1-10}$ alkanol, $C_{1-10}$ alkanethiol, aryl, heterocyclic radicals (e.g. heteroaryl), $C_{1-3}$ alkoxy $C_{1-3}$ alkyl, di-$C_{1-3}$ alkoxy $C_{1-3}$ alkyl, $C_{1-3}$ alkyloxy aryl $C_{1-3}$ alkyl, $C_{1-3}$ alkyl aryl, $C_{1-3}$ alkyl sulfanyl $C_{1-3}$ alkyl, $C_{1-3}$ alkyl aryl sulfanyl $C_{1-3}$ alkyl, aryloxy $C_{1-3}$ alkyl, N,N—$C_{1-3}$ dialkyl $C_{1-3}$ alkylamine, N—$C_{1-3}$ alkyl $C_{1-3}$ alkylamine, aryl sulphonyl $C_{1-3}$ alkyl or $R_1$ and $R_2$ form together a cycloalkyl group or a heterocyclic group.

The diprotic acid is preferably added in an amount of from 2 to 15 equivalents (related to compound (II)), preferably in an amount of 5 to 15 equivalents and more preferably in an amount of 10 to 15 equivalents. The use of a diprotic acid having a negative pKa is advantageous as it permits ring closure while it has been observed (see comparative examples below) that Lewis acids such as $BF_3$ leads to side reactions in addition to the ring closure product and that monoprotic mineral acids such as HCl do not enable the ring closure. The reaction can be performed in bulk (without the addition of a solvent) or with the addition of an organic solvent. Preferably, an organic solvent is added. It has been observed that the ring closure reaction operates in better yields when compound (II) is diluted in an organic solvent. Examples of organic solvents are $C_5$-$C_{12}$ hydrocarbons such as e.g. n-octane. The presence of an organic solvent is preferred as it increases the yield of the ring closure reaction.

The ring closure reaction can be performed at any temperature from 0° C. to reflux of the reaction media. For instance the reaction can be performed between 10 and 50° C. or between 18 and 27° C. Typically, the reaction may be performed at room temperature.

The ring closure reaction can be performed at different reaction time, for instance from 30 min to 24 hours. For instance the reaction can be performed overnight. Typically, the reaction may be completed after 1 to 2 hours reaction.

In an embodiment of the first aspect of the present preferred embodiments, $R_1$ and $R_2$ are different. This is advantageous as it decreases the tendency of crystallization and increases their amorphous character. An asymmetric substitution permits the incorporation of one or more functionality in the same molecule e.g. each of $R_1$ and $R_2$ can have one or more functionality. For instance, $R_1$ and $R_2$ could incorporate different functionalities in the molecule selected from a group that serve to increase the solubility of the molecule, a group that provide an ion, a group that comprises a dye or a group for self assembly (e.g. an alkanethiol). For instance, $R_1$ could serve to increase the solubility of the molecule while $R_2$ could provide an ion. Other possibilities include the provision of a dye on $R_1$ and a solubilizing group on $R_2$ or of a group for self assembly (e.g. an alkanethiol) and another group having another function. In a preferred embodiment at least one of $R_1$ and $R_2$ is an alkyl group.

In an embodiment of the first aspect of the present preferred embodiments, the compound having the general formula (II):

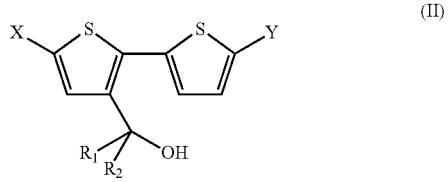

(II)

may be prepared by the reaction of a compound having the general formula (III):

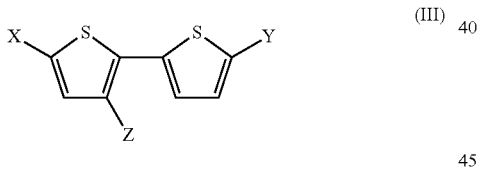

(III)

wherein Z is a halogen or a pseudo-halogen and wherein X and Y are independently selected from the group consisting of hydrogen, chloro, bromo, iodo, boronic acid, boronate esters, borane, pseudohalogen and organotin. The case where X=Y=H is preferred, with a base, then with a compound having the general formula $R_1(CO)R_2$, wherein $R_1$ and $R_2$ are as defined above (including $R_1$ and $R_2$ shown in compounds IIa to IIdj below).

The halogen is preferably selected from the group consisting of Br, Cl or I and is preferably bromine.

In an embodiment of the first aspect of the present preferred embodiments, the base may be a strong base (e.g. having a pKa of at least 13), preferably an alkyl lithium base and more preferably n-butyllithium, sec-butyllithium or tert-butyllithium. Also usable are organometallic reagents such as Grignard reagents and organozinc In an embodiment, the preparation of (II) from (III) may involve the preparation of an organometallic compound of formula (XVI):

(XVI)

by reacting compound (III) with a metal M such as Mg or Zn instead of reacting it with a base. The compound (XVI) may thereafter be reacted with a compound having the general formula $R_1(CO)R_2$ in the presence of a base, wherein $R_1$ and $R_2$ are as defined above (including $R_1$ and $R_2$ shown in compounds IIa to IIdj).

In an embodiment of the first aspect of the present preferred embodiments, the amount of base may be comprised between 0.7 and 1.3 equivalents, preferably between 0.9 and 1.1 eq and more preferably between 0.95 and 1.05 eq. Most preferably 1 equivalent of base is used.

In an embodiment of the first aspect of the present preferred embodiments, the amount of $R_1(CO)R_2$ is comprised between 0.7 and 1.3 equivalents, preferably between 0.9 and 1.1 eq and more preferably between 0.95 and 1.05 eq. Most preferably 1 equivalent of $R_1(CO)R_2$ is used. The ketone determines which groups $R_1$, $R_2$ will be present in product (II) and (I). The wide range of possible ketones provides a broad scope of opportunities in functionalizing cyclopentadithiophenes.

In a second aspect, the present preferred embodiments relates to a chemical compound having the general formula (II):

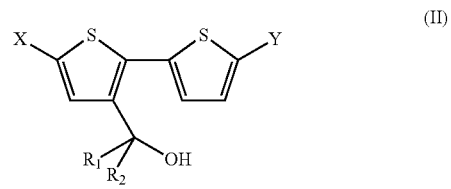

(II)

wherein $R_1$, $R_2$, X and Y are as defined in any embodiment of the first aspect.

In embodiments of the second aspect of the present preferred embodiments, the chemical compound according to the second aspect of the present preferred embodiments may be selected from the formulas below (but not limited to them as other ketones can be synthesized and then used in a reaction with compound (III)):

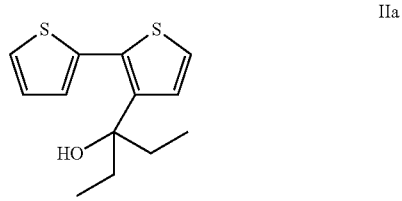

IIa

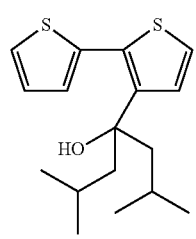 IIb
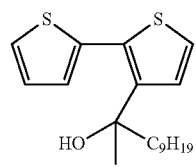 IIc
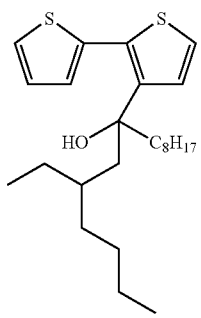 IId
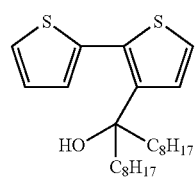 IIe
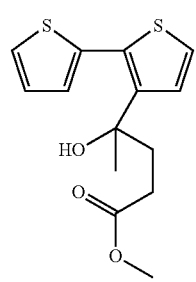 IIf
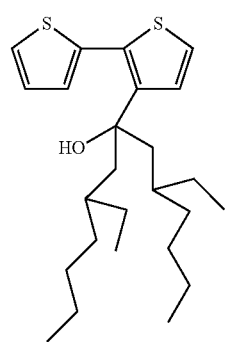 IIg
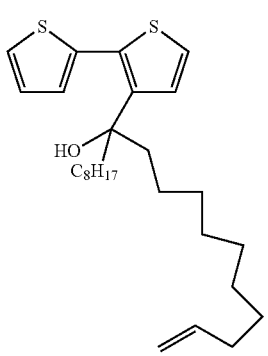 IIh
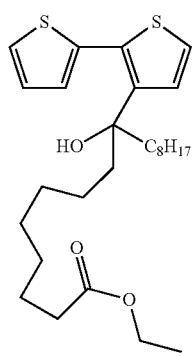 IIi
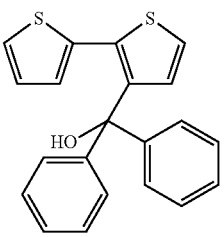 IIj
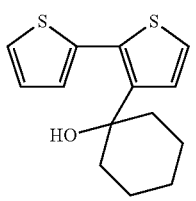 IIk
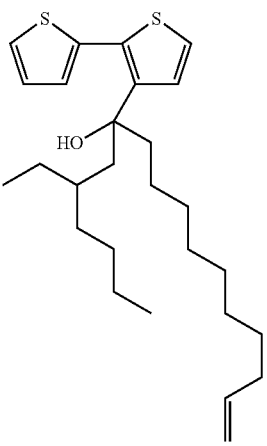 IIm

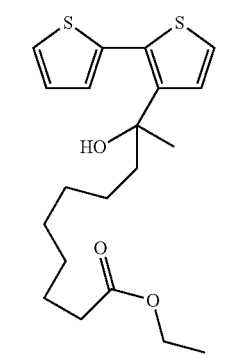
IIn
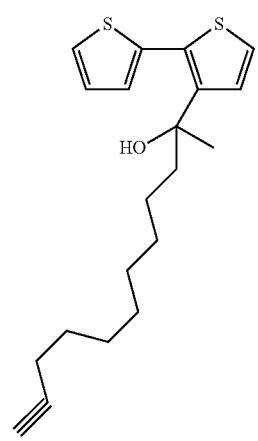
IIo
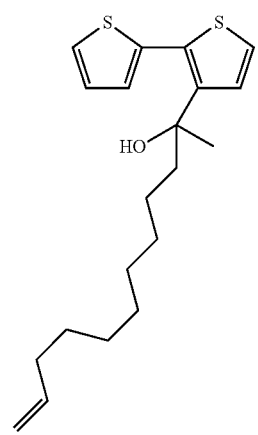
IIp
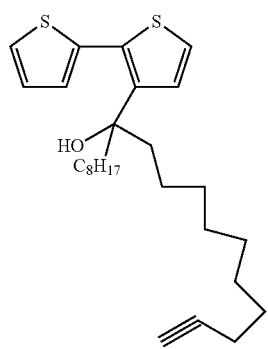
IIq
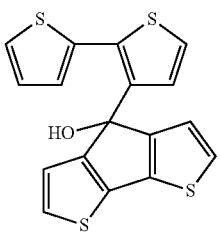
IIr
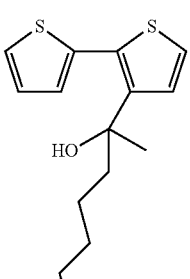
IIs
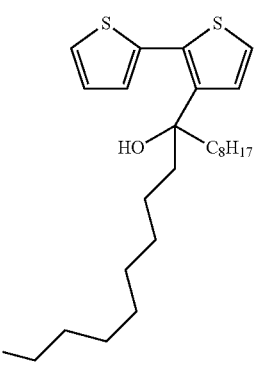
IIt
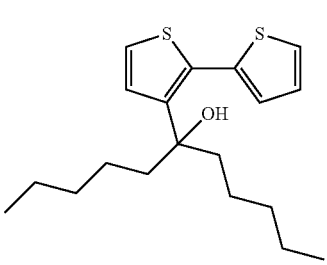
IIu
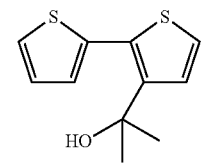
IIv
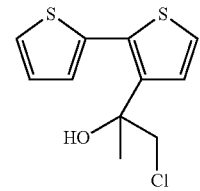
IIw

| | |
|---|---|
| 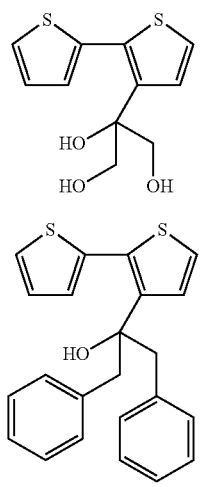 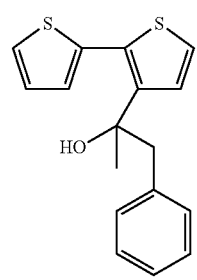 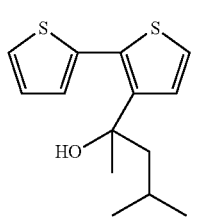 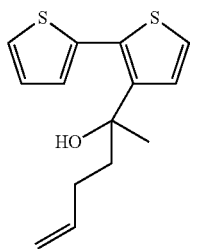 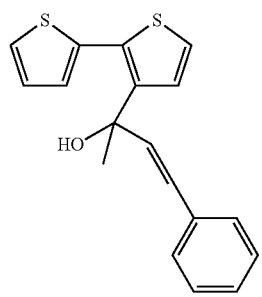 | IIx IIy IIz IIaa IIab IIac 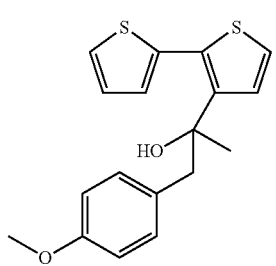 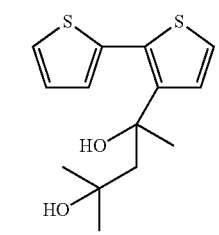 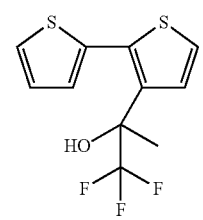 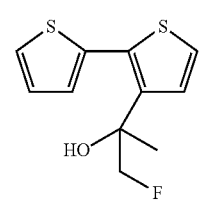 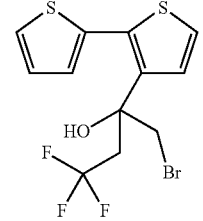 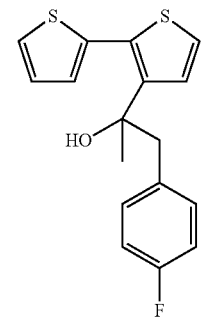 IIad IIae IIaf IIag IIah IIai |

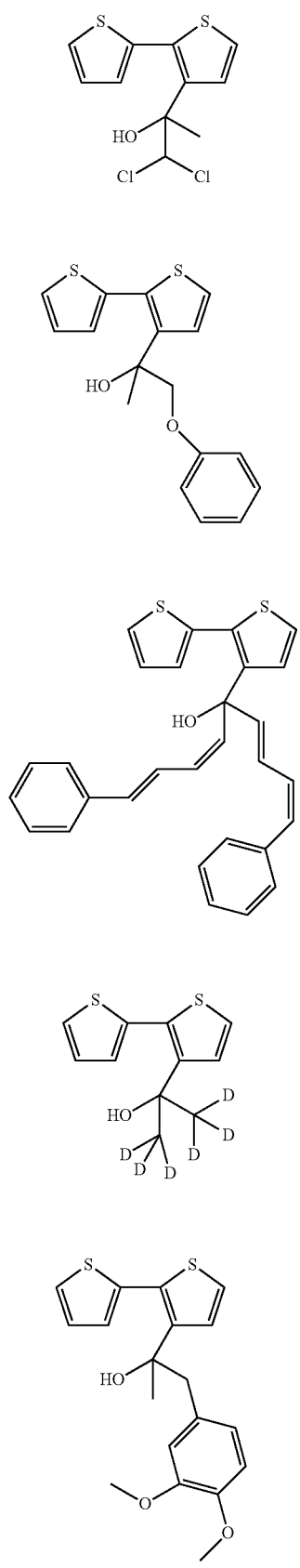

25
-continued
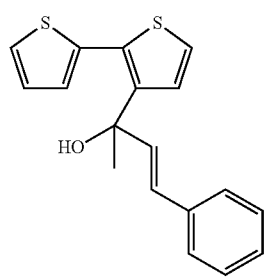
IIau
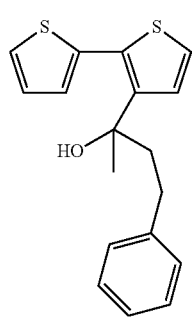
IIav
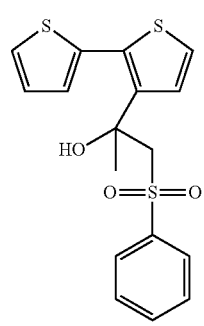
IIaw
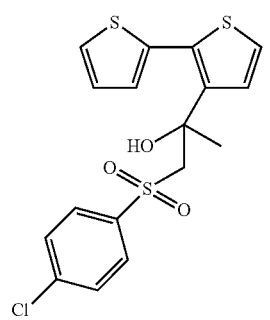
IIax
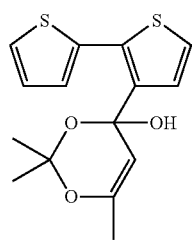
IIay
26
-continued
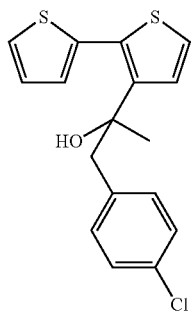
IIaz
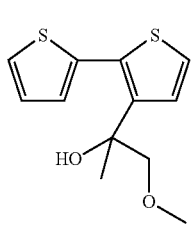
IIba
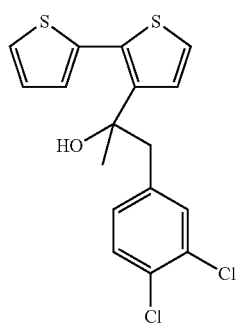
IIbb
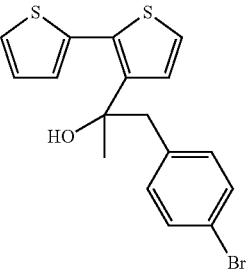
IIbc
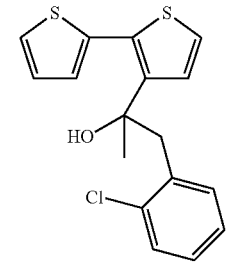
IIbd
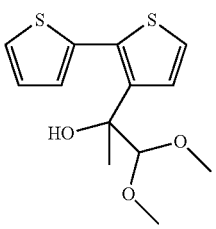
IIbe

| | |
|---|---|
| 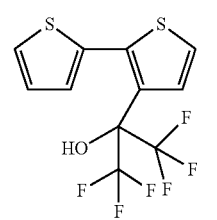 IIbf | 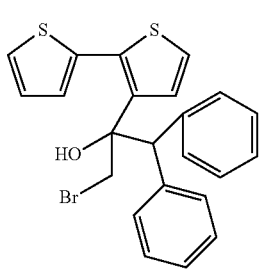 IIbl |
| 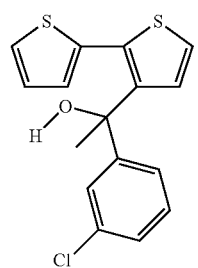 IIbg | 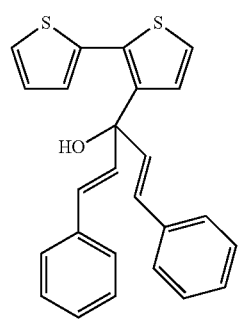 IIbm |
| 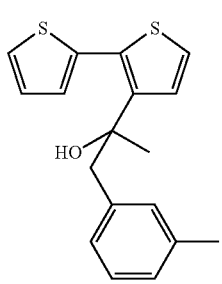 IIbh | 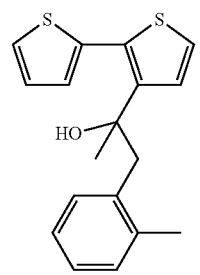 IIbn |
| 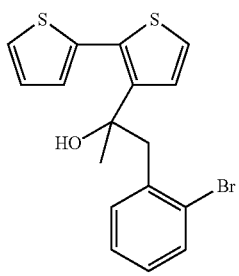 IIbi | 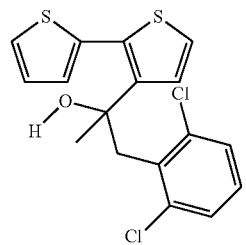 IIbo |
| 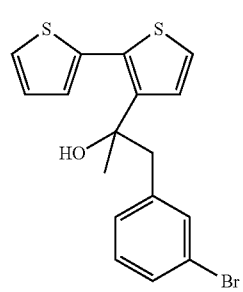 IIbj | 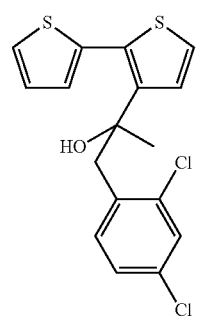 IIbp |
| 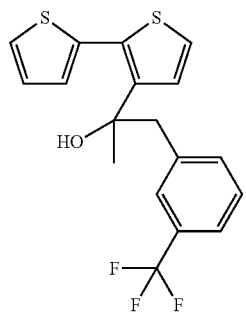 IIbk | |

-continued
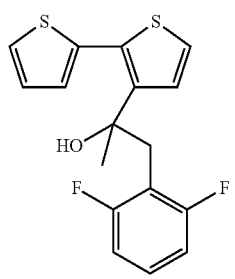 IIbq
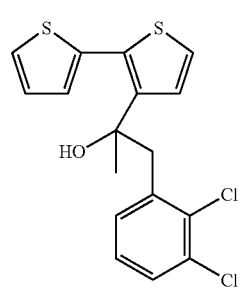 IIbr
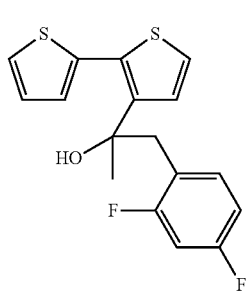 IIbs
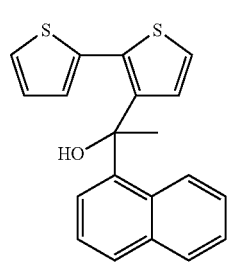 IIbt
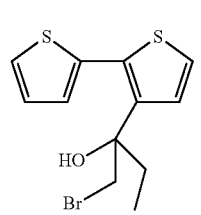 IIbu
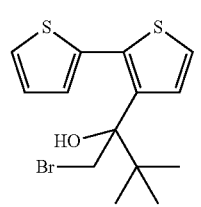 IIbv
-continued
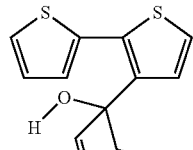 IIbw
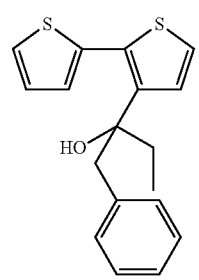 IIbx
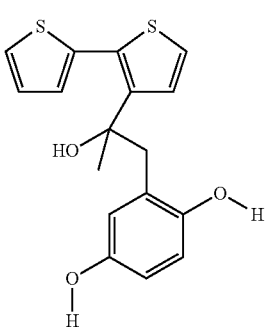 IIby
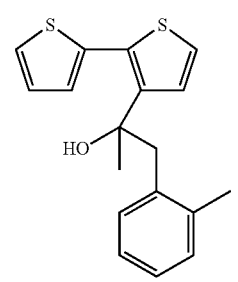 IIbz
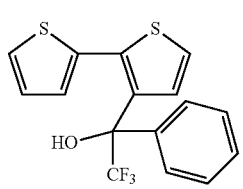 IIca
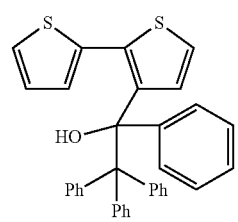 IIcb
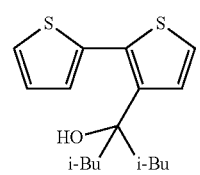 IIcc -continued
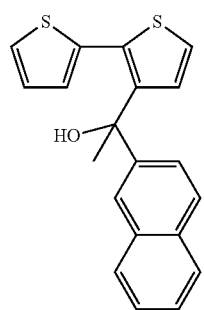
IIcd
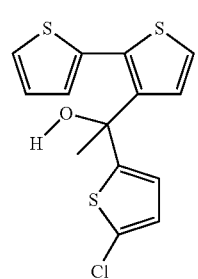
IIce
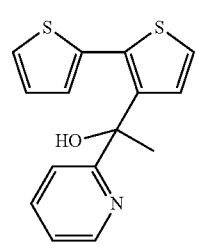
IIcf
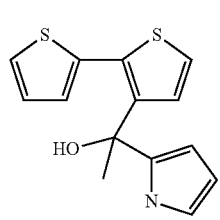
IIcg
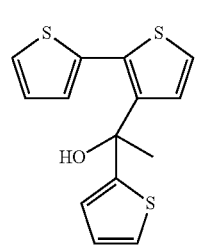
IIch
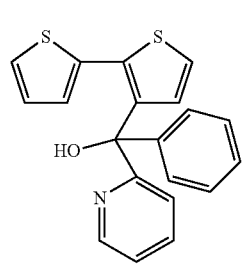
IIci
-continued
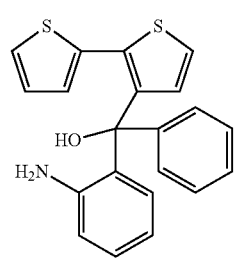
IIcj
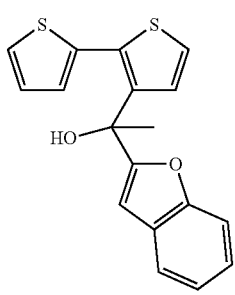
IIck
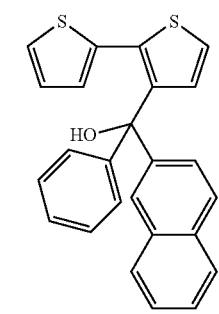
IIcl
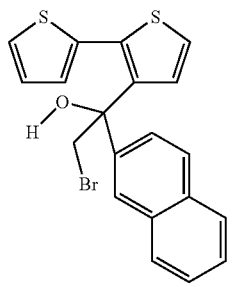
IIcm
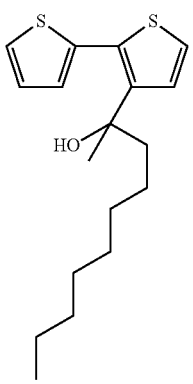
IIcn -continued
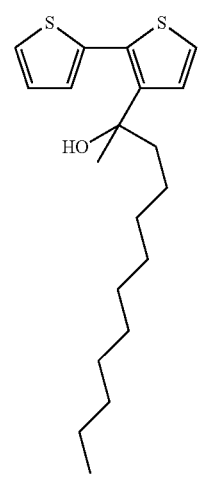
IIco
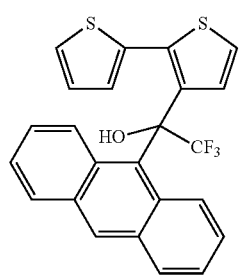
IIcp
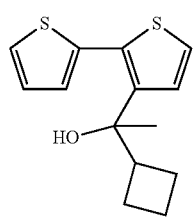
IIcq
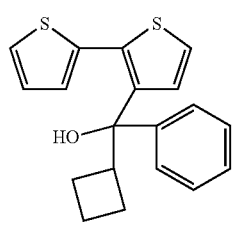
IIcr
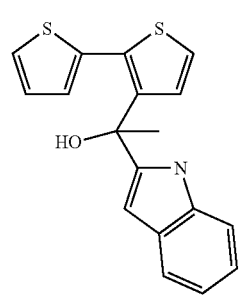
IIcs
-continued
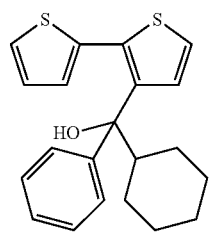
IIct
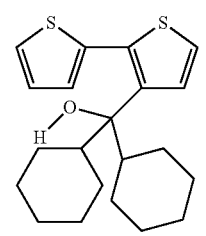
IIcu
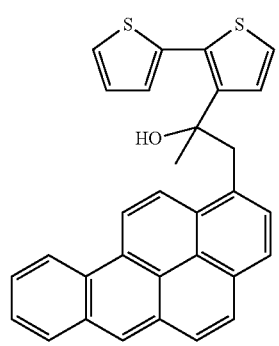
IIcv
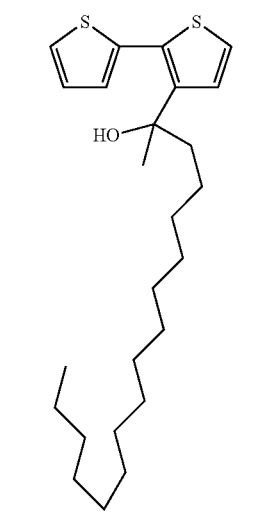
IIcw
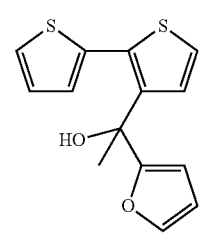
IIcx

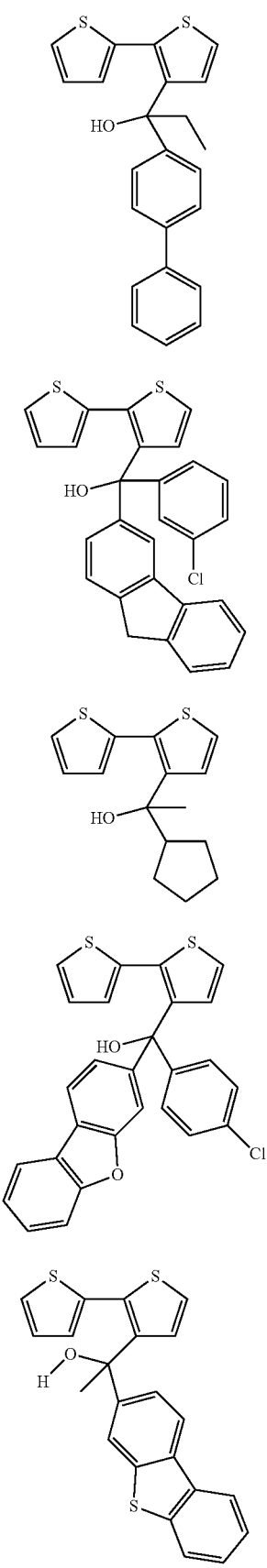
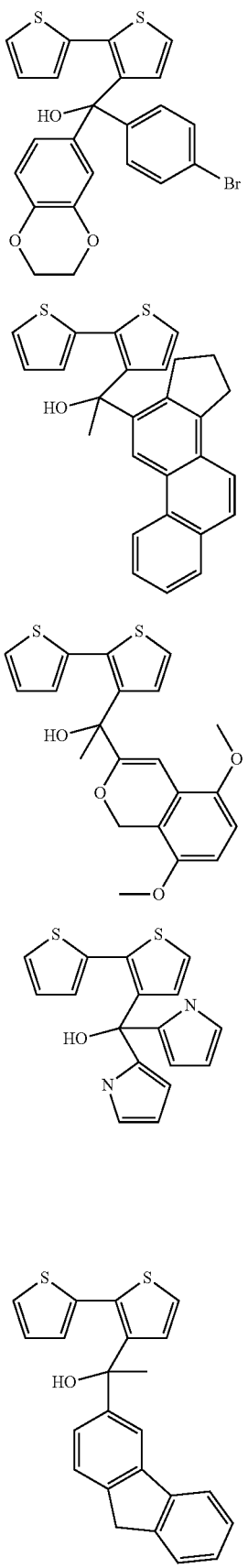

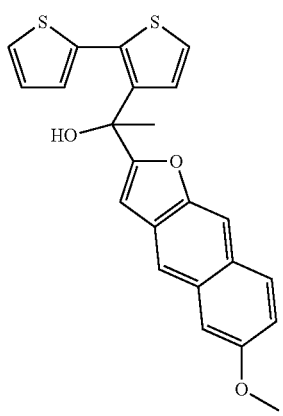

IIdi

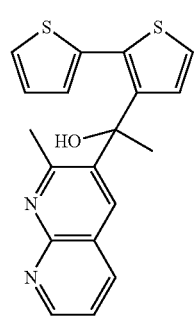

IIdj

In a third aspect, the present preferred embodiments relates to molecules of the general formula (I)

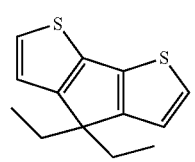

(I)

wherein $R_1$ and $R_2$ are as defined in any embodiment of the first aspect of the present preferred embodiments and wherein X and Y are independently selected from the group consisting of hydrogen, chloro, bromo, iodo, boronic acid, boronate esters, borane, pseudohalogen and organotin.

In embodiments of the third aspect of the present preferred embodiments, the chemical compound according to the second aspect of the present preferred embodiments may be selected from the formula below (but not limited to them):

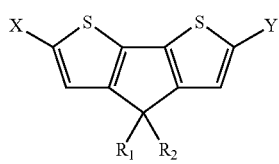

Ia

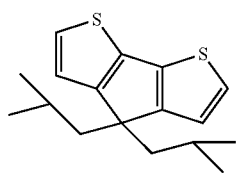

Ib

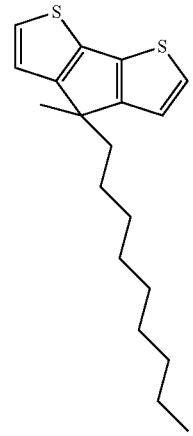

Ic

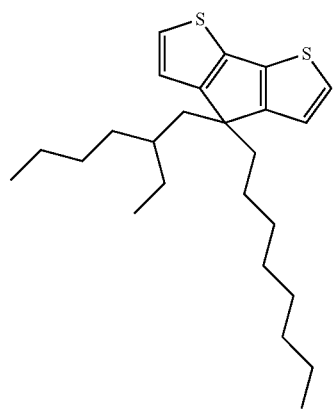

Id

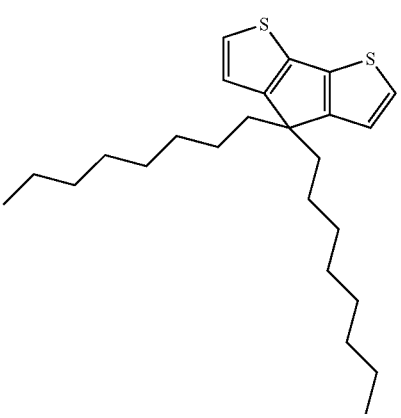

Ie

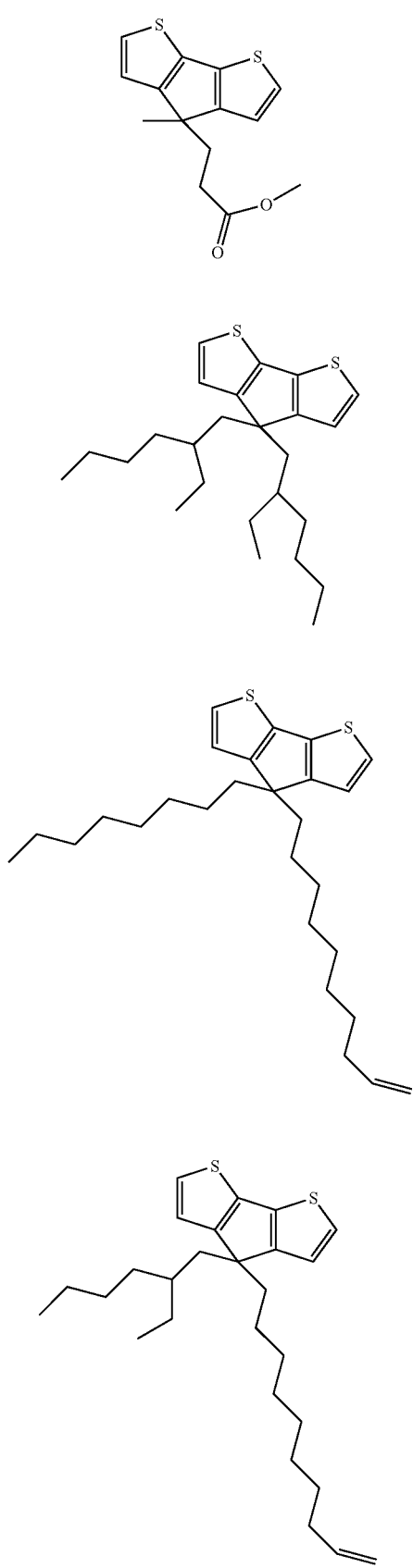
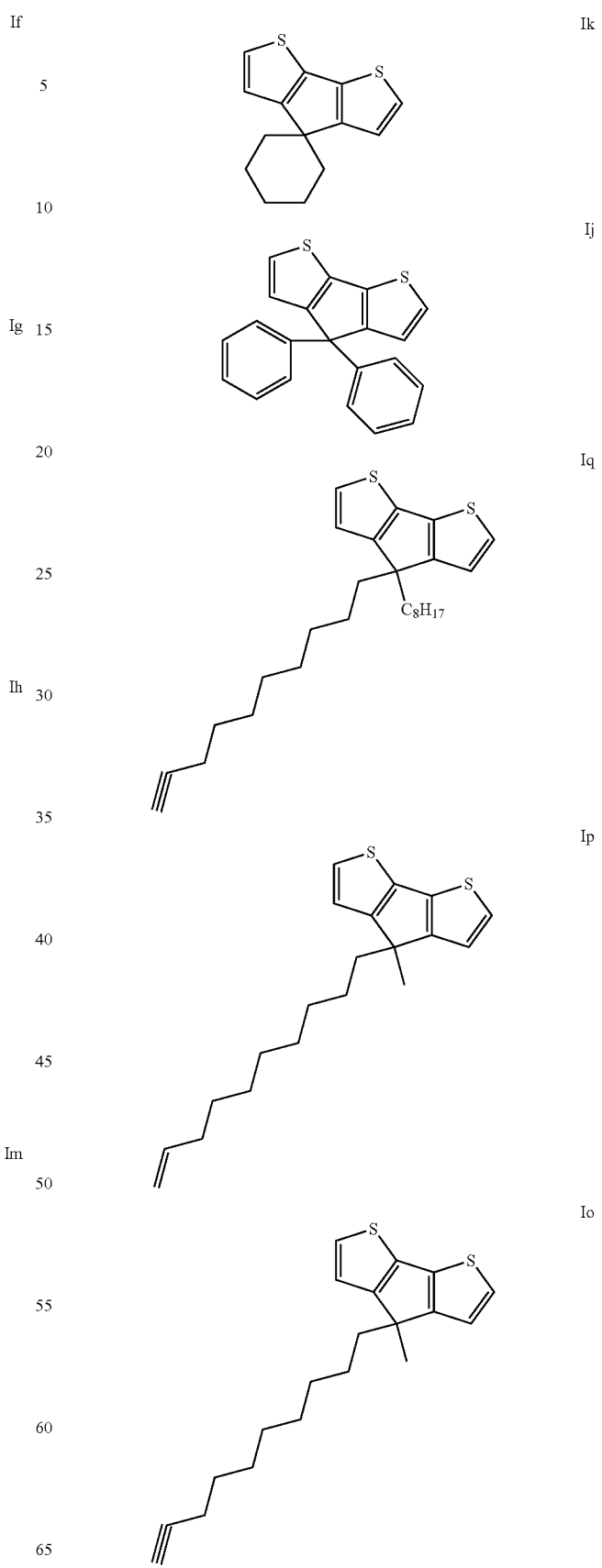

In
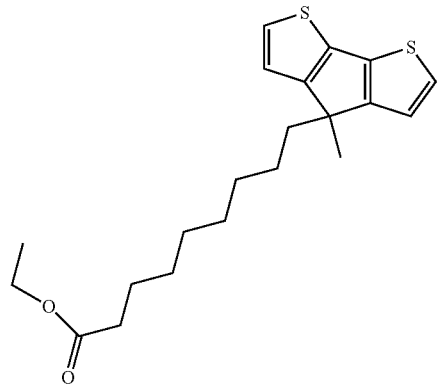
Ii
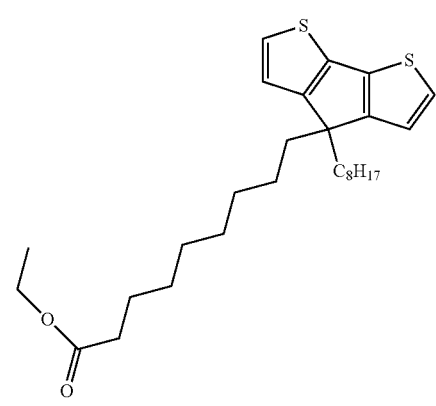
Is
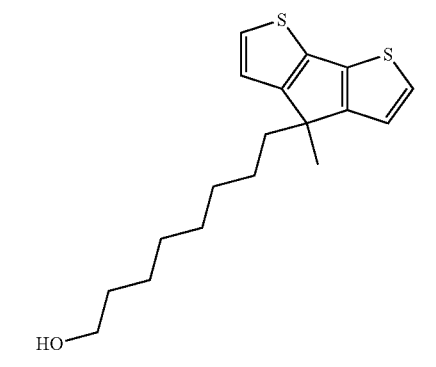
It
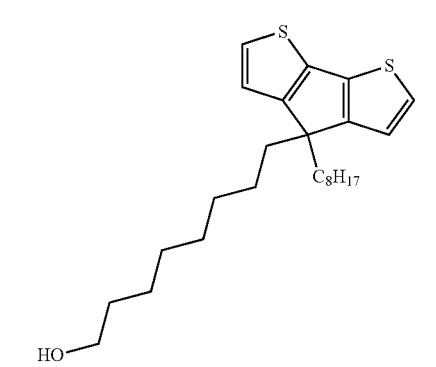
Ir
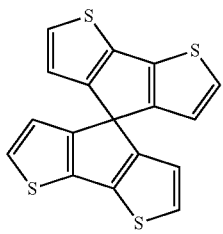
Iu
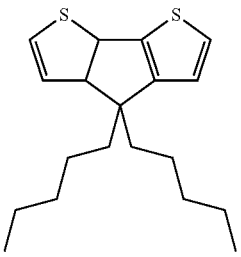
Iv
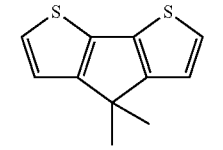
Iw
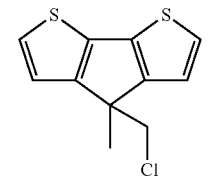
Ix
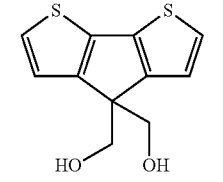
Iy
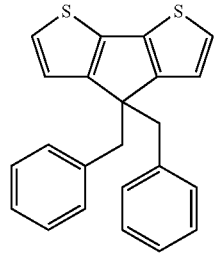
Iz
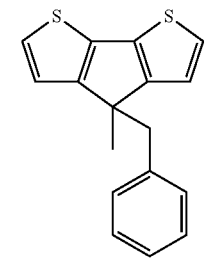

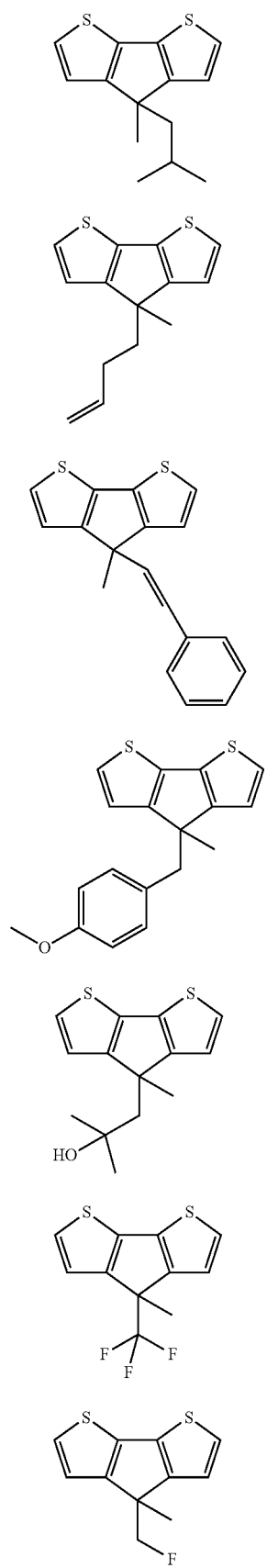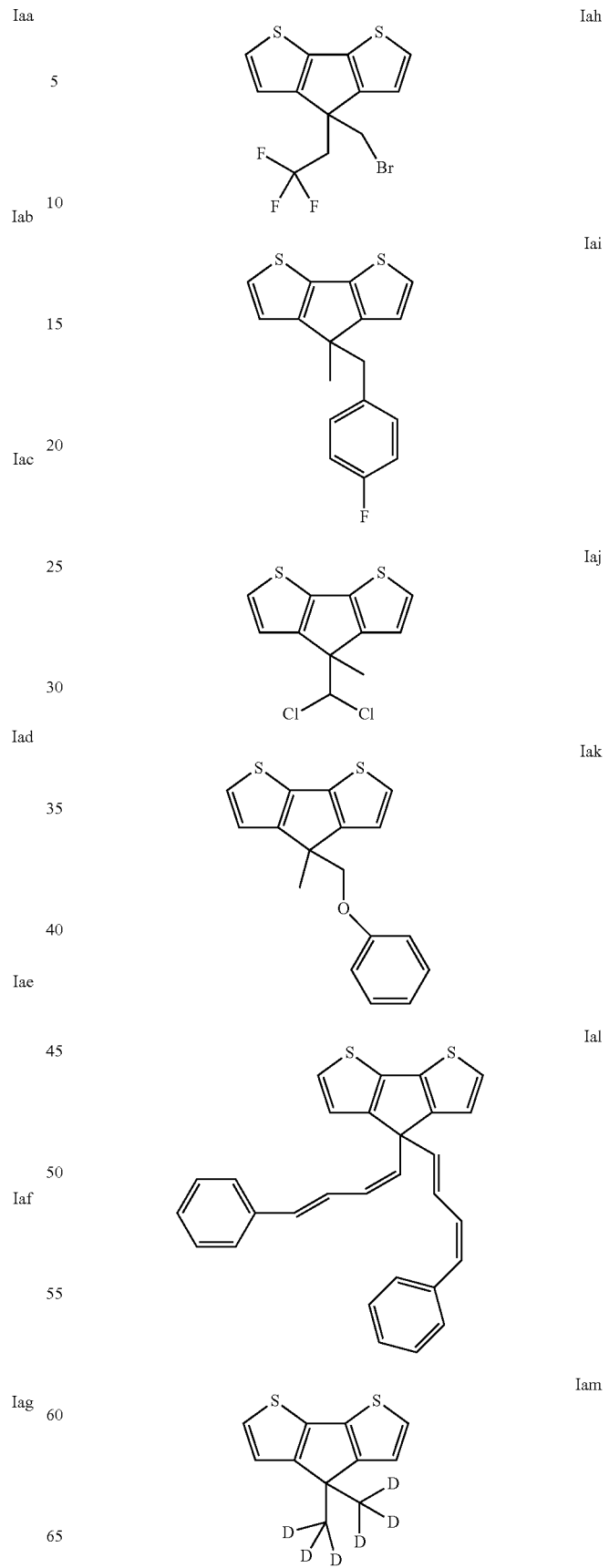

Ian
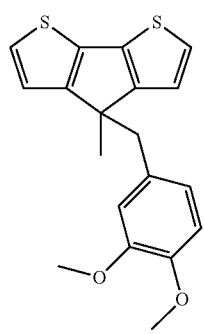
Iao
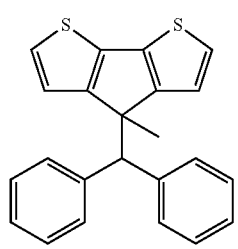
Iap
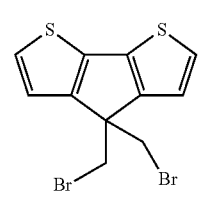
Iaq
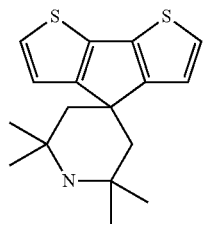
Iar
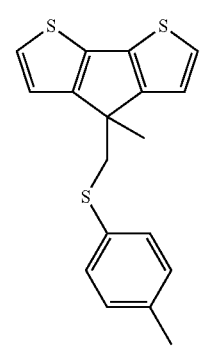
Ias
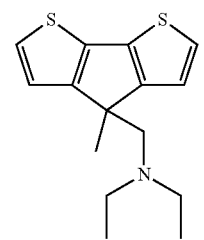
Iat
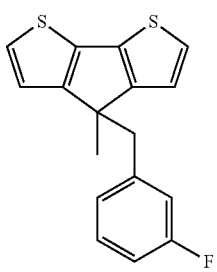
Iau
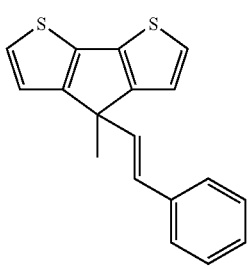
Iav
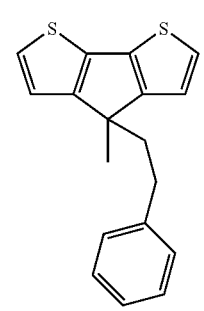
Iaw
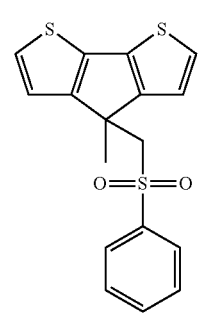
Iax
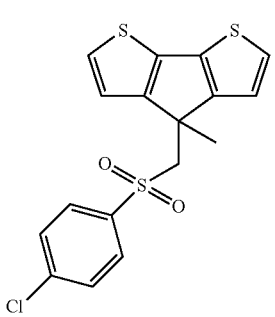

| | |
|---|---|
| Iay 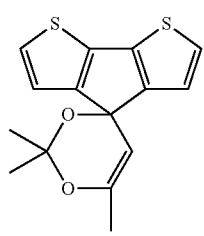 | Ibe 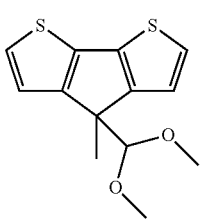 |
| Iaz 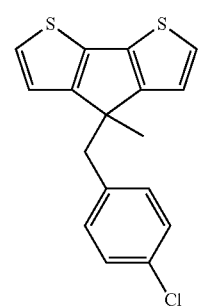 | Ibf 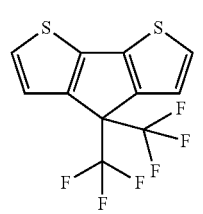 |
| Iba 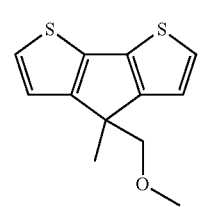 | Ibg 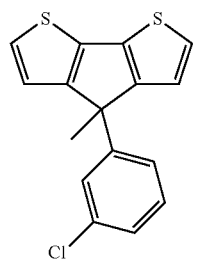 |
| Ibb 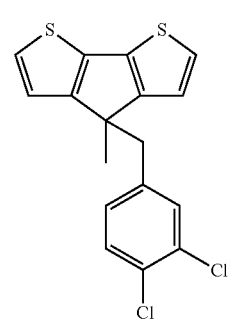 | Ibh 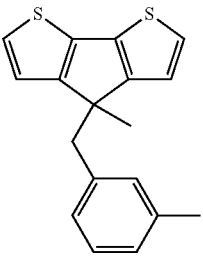 |
| Ibc 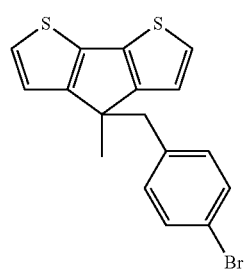 | Ibi 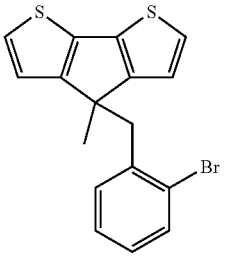 |
| Ibd 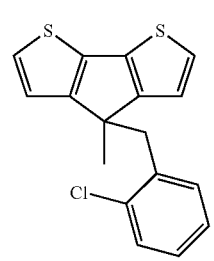 | Ibj 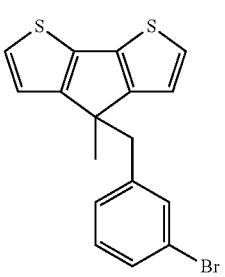 |

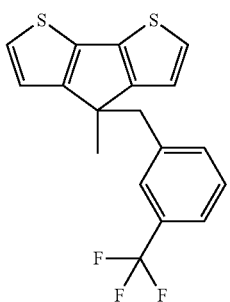 Ibk
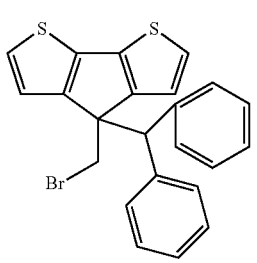 Ibl
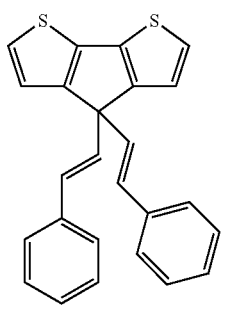 Ibm
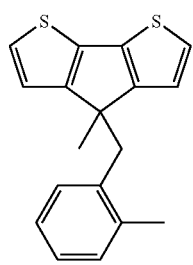 Ibn
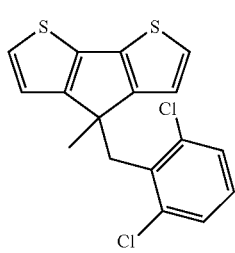 Ibo
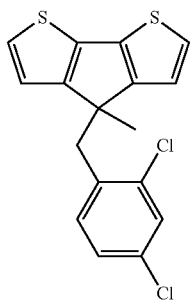 Ibp
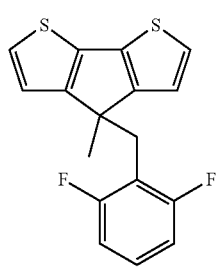 Ibq
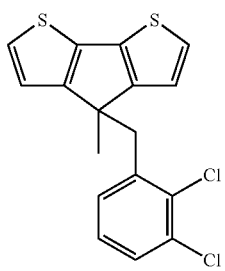 Ibr
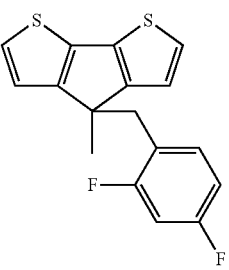 Ibs
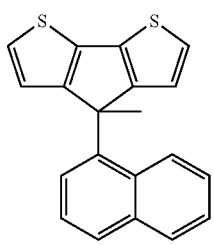 Ibt
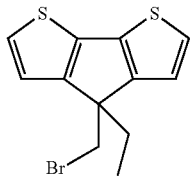 Ibu

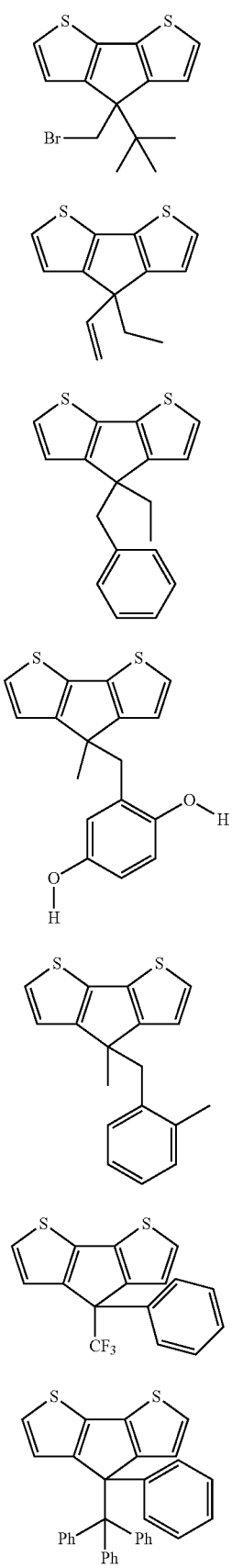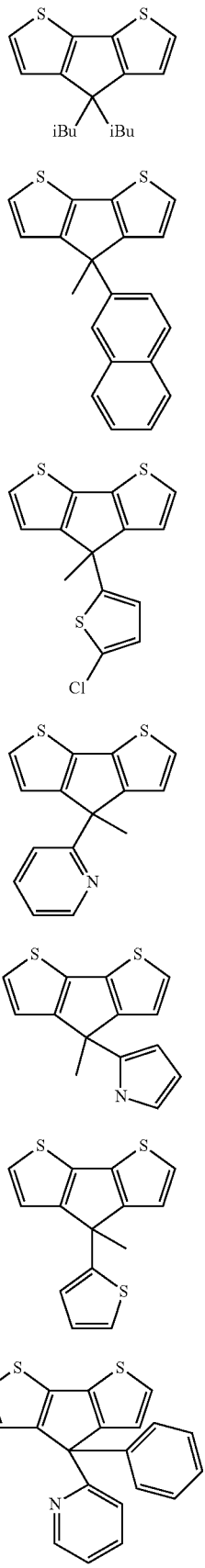

-continued
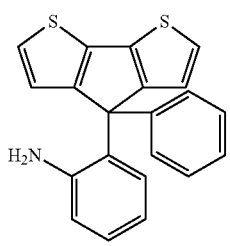
Icj
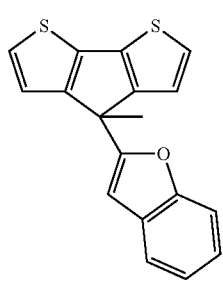
Ick
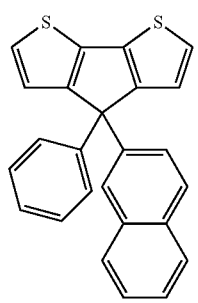
Icl
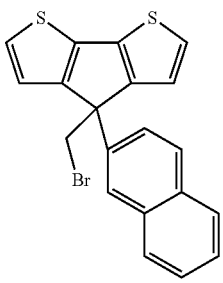
Icm
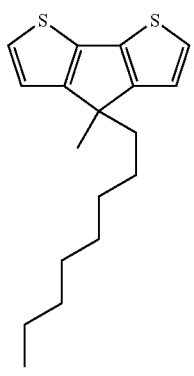
Icn
-continued
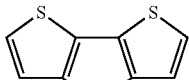
Ico
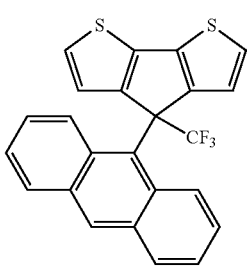
Icp
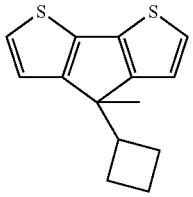
Icq
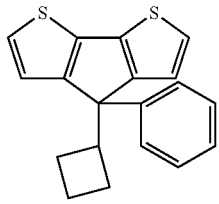
Icr
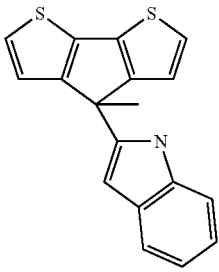
Ics
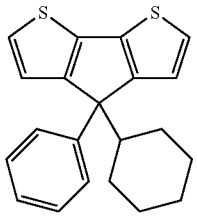
Ict

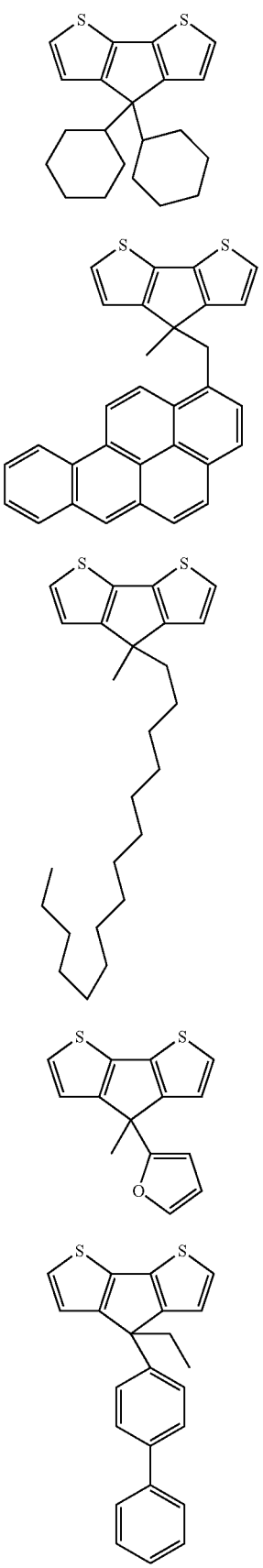
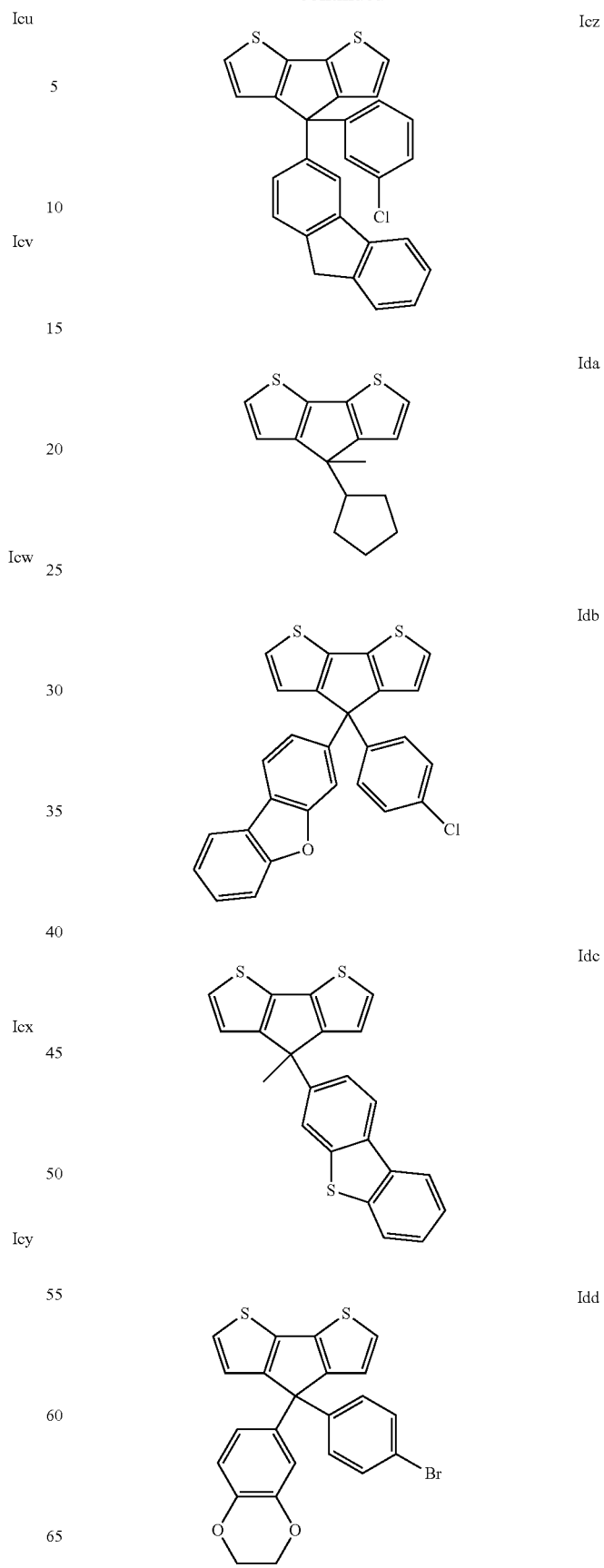

Ide 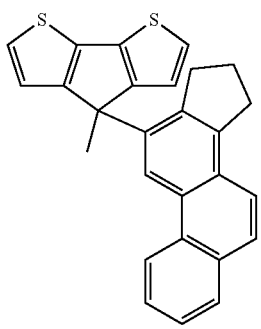

Idf 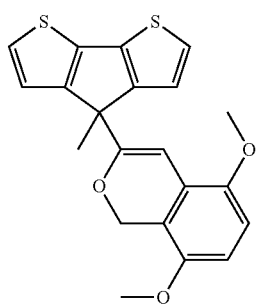

Idg 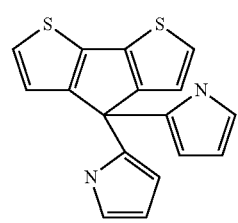

Idh 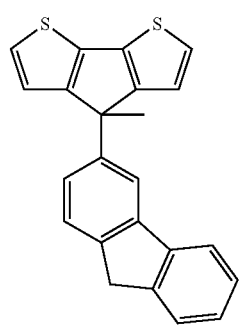

Idi 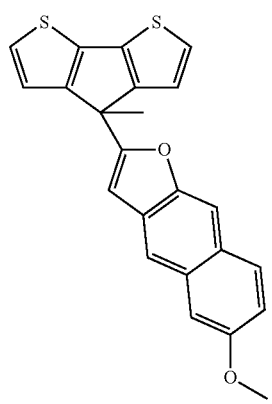

Idj 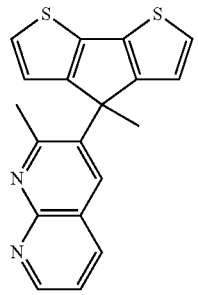

As mentioned above, in an embodiment of the third aspect, the present preferred embodiments relates to a molecule having the general formula below:

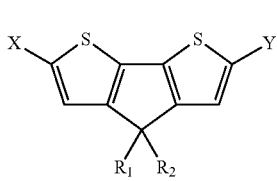
(I)

wherein $R_1$ and $R_2$ are as defined for any embodiment of the third aspect (including $R_1$ and $R_2$ as shown in any of examples Ia to Idj) and wherein X and Y are independently selected from the group consisting of hydrogen, chloro, bromo, iodo, boronic acid, boronate esters, boranes, pseudohalogens and organotin. Obtaining X and/or Y other than H can be done for instance by one of the methods described below applied on a compound (I) having at least X=H or Y=H and preferably both X and Y=H.

Methods leading to the chlorination, bromination or iodination of aromatic compounds are well known in de art (Advanced Organic Chemistry, part B, 5$^{th}$ ed., p. 1008-1014, F. Carey, R. Sundberg). Brominating can for instance be obtained as follow. Protected from light, a solution of N-Bromosuccinimide (NBS) in an appropriate solvent (e.g. DMF) can be added dropwise to a solution of cyclopentadithiophene derivative (I) in another or the same appropriate solvent (e.g. DMF). Molecular bromine, chlorine or iodine can also be used to achieve halogenations of the cyclopentadithiophene derivative (I).

Methods enabling the replacement of a halide group by a boronic acid, a boronic ester or a borane are well known in the art (Advanced Organic Chemistry, part B, 5$^{th}$ ed., p. 784-786, F. Carey, R. Sundberg).

Methods enabling the replacement of a halide group by an organotin are well known in the art (Advanced Organic Chemistry, part B, 5$^{th}$ ed., p. 834, last §, F. Carey, R. Sundberg).

Methods enabling the introduction of a pseudohalogen on an aromatic group are equally well known in the art. For instance, it can proceed first via a nitration (e.g. of compound (I)), followed by a reduction to an amino, followed by a diazotation, followed by substitution by an alcohol, followed by reaction with e.g. the sulfonic acid of the pseudohalogen (e.g. para-toluene sulfonic acid).

EXAMPLES

Unless otherwise stated, all reagents and chemicals were obtained from commercial sources and used without further purification. Diethyl ether was dried by distillation from sodium/benzophenone. NMR spectra were recorded with a Varian Inova 300 spectrometer at 300 MHz for $^1$H NMR and at 75 MHz for $^{13}$C NMR using a 5 mm probe. Chemical shifts (δ) in ppm were determined relative to the residual CHCl$_3$ absorption (7.26 ppm) and to the $^{13}$C resonance shift of CDCl$_3$ (77.70 ppm).

Comparative Example 1

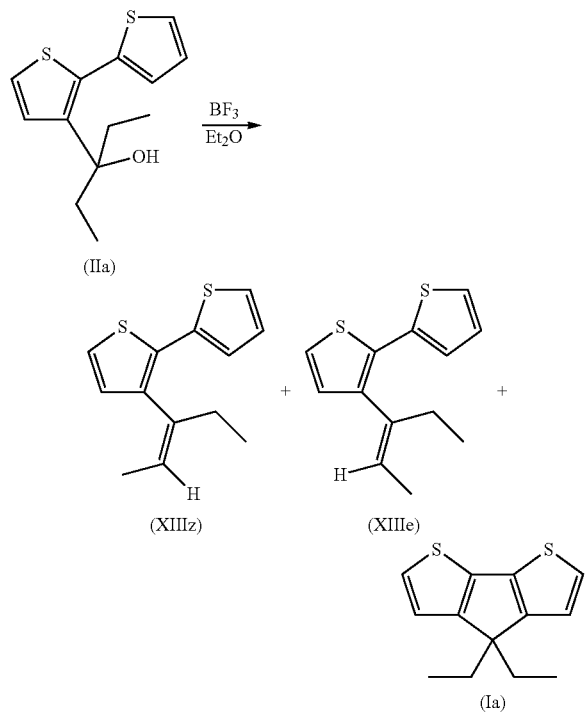

(XIIIz)+(XIIIe) 3-(pent-2-en-3-yl)-2,2'-bithiophene+ 4,4'-diethyl-4H-cyclopenta(1,2-b:5,4-b')-dithiophene Normal Addition 3-(2,2'-bithiophene-3-yl)pentan-3-ol (0.100 g, 0.40 mmol) (IIa) was dissolved in dichloromethane (60 mL) and treated with an excess of boron trifluoride etherate (4.02 mL, 32 mmol). The solution was stirred for 3 h, and then a mixture of ethanol/water (2:1) was added. The organic layer was dried over MgSO$_4$ and the solvent was removed under vacuum. The residue was purified by column chromatography on silica (n-Hexane). (0.051 g, 55%). Due to very similar polarities compound (Ia) cannot be isolated from the two isomers (XIIIz) and (XIIIe). (XIIIz) and (XIIIe) are formed as main products in a 80:20 ratio compared to (Ia).

Reverse Addition

An excess of boron trifluoride etherate (4.02 mL, 32 mmol) was dissolved in dichloromethane (50 mL). A solution of 3-(2,2'-bithiophene-3-yl)pentan-3-ol (IIa) (0.100 g, 0.40 mmol) in dichloromethane (10 mL) was then added to the reaction mixture. The solution was stirred for 3 h, and then a mixture of ethanol/water (2:1) was added. The organic layer was dried over MgSO$_4$ and the solvent was removed under vacuum. The residue was purified by column chromatography on silica (n-Hexane). (0.051 g, 55%). Due to very similar polarities compound (Ia) cannot be isolated from the two isomers (XIIIz) and (XIIIe). (XIIIz) and (XIIIe) are formed as main products in a 80:20 ratio compared to (Ia).

This reaction has been performed at various temperature and reaction times. These conditions are summarized in the table below. None of them led to (Ia) as pure product.

TABLE 1

| BF$_3$.Et$_2$O | solvent | Conc | React. time | T° C. | TLC results | 1H NMR results (5.41 ppm/ quartet) | Presence of alkene isomers |
|---|---|---|---|---|---|---|---|
| 1 eq. | CH$_2$Cl$_2$ | 0.010 | 12 h | r.t. | 1 spot | visible | yes |
| 80 eq. | CH$_2$Cl$_2$ | 0.010 | 3 h | r.t. | 1 spot | visible | yes |
| 80 eq. reverse addition | CH$_2$Cl$_2$ | 0.010 | 3 h | r.t. | 1 spot | visible | yes |
| 160 eq. | CH$_2$Cl$_2$ | 0.010 | 3 h | r.t. | 1 spot | visible | yes |

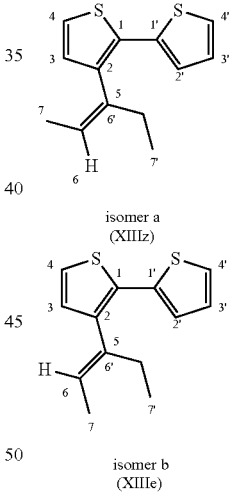

isomer a (XIIIz)

isomer b (XIIIe)

TABLE 2

| Proton (XIIIz) | Shift (ppm) | Carbon (XIIIz) | Shift (ppm) | Proton (XIIIe) | Shift (ppm) | Carbon (XIIIe) | Shift (ppm) |
|---|---|---|---|---|---|---|---|
| H2' | 7.17 (dd) | C2' | 125.60 | H2' | 7.15 (dd) | C2' | 126.32 |
| H3 | 6.77 (d) | C3 | 130.80 | H3 | 6.85 (d) | C3 | 130.80 |
| H3' | 6.98 (dd) | C3' | 127.68 | H3' | 6.98 (dd) | C3' | 127.48 |
| H4 | 7.16 (d) | C4 | 123.64 | H4 | 7.12 (d) | C4 | 123.54 |
| H4' | 7.20 (dd) | C4' | 125.40 | H4' | 7.20 (dd) | C4' | 125.68 |
| H6 | 5.62 (q) | C6 | 124.44 | H6 | 5.55 (q) | C6 | 126.60 |
| H6' | 2.26 (q) | C6' | 31.67 | H6' | 2.32 (q) | C6' | 24.78 |
| H7 | 1.45 (d) | C7 | 15.40 | H7 | 1.74 (d) | C7 | 14.31 |
| H7' | 0.99 (t) | C7' | 13.52 | H7' | 0.91 (t) | C7' | 14.83 |

TABLE 2-continued

| T1 | Carbon (XIIIz) | Shift (ppm) | T1 | Carbon (XIIIe) | Shift ppm |
|---|---|---|---|---|---|
| 29.34 | C5 | 138.08 | 26.83 | C5 | 137.27 |
| 45.48 | C2 | 137.70 | 46.16 | C2 | 141.36 |
| 57.03 | C1' | 136.53 | 60.86 | C1' | 136.65 |
| 68.81 | C1 | 131.65 | 61.78 | C1 | 131.04 |

Comparative Example 2

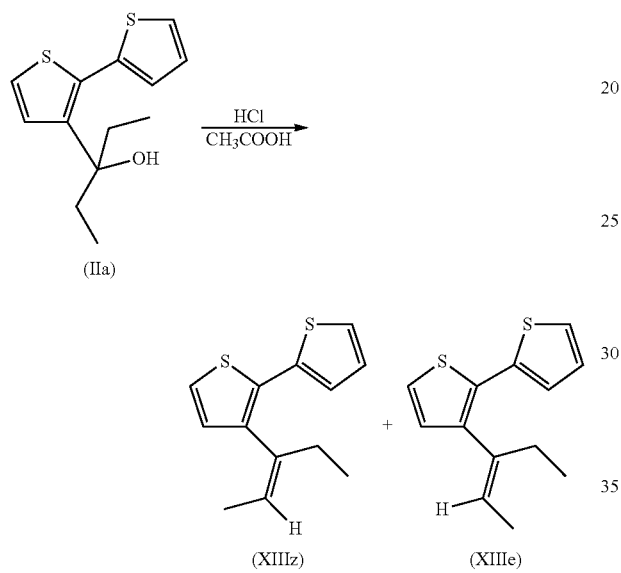

(XIIIz)+(XIIIe) 3-(pent-2-en-3-yl)-2,2'-bitiophene 3-(2,2'-bithiophene-3-yl)pentan-3-ol (IIa) (0.100 g, 0.40 mmol) was dissolved in acetic acid (69 mL). A solution of concentrated HCl (0.28 mL) in acetic acid (15 mL) was added via syringe to the reaction mixture. The solution was refluxed for 4 h followed by an extraction with chloroform, washing and drying over $MgSO_4$. The solvent was removed in vacuo. The residue was purified by column chromatography on silica (n-Hexane). (0.070 g, 75%).

This reaction has been performed at various temperature and reaction times. These conditions are summarized in the table below. None of them led to (Ia).

TABLE 3

| HCl (37%) | solvent | Conc. | React. time | T °C. | TLC results | 1H NMR results (5.41 ppm/quartet) | Presence of alkene isomers |
|---|---|---|---|---|---|---|---|
| 0.28 mL | Acetic acid | 0.005 | 4 h | reflux | 1 spot | visible | yes |
| 0.28 mL | Acetic acid | 0.005 | 12 h | reflux | 1 spot | visible | yes |

Example 1

3-Bromo-2,2'-bithiophene (IIIa)

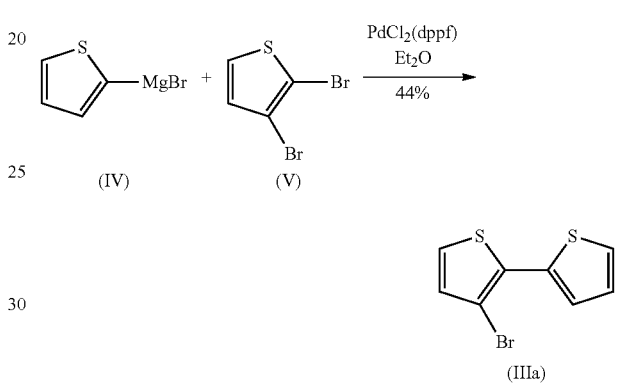

This compound was synthesized according to a procedure analogous to the one described in A. Facchetti et al., *J. Am. Chem. Soc.*, 126, 2004, 13480-13501. A Grignard solution of 2-bromothiophene (8.05 mL, 83 mmol) and Mg (2.42 g, 0.10 mol) in dry diethylether (150 mL) was prepared (finally refluxing for 45 minutes under $N_2$). The Grignard solution was added dropwise under $N_2$ over 1 h to a stirred and cooled (about −5° C.) suspension of Pd(dppf)$Cl_2$ (0.41 g, 0.83 mmol) and 2,3-dibromothiophene (V) (9.10 mL, 83 mmol) in dry diethylether (120 mL). After further stirring at 0° C. for 3 h, methanol (10 mL) was added (to quench the reaction) and the mixture was filtered through a 2 cm $MgSO_4$/silica gel double layer. After further eluting of the double layer with dry diethyl ether (30 mL) the solvent was evaporated under reduced pressure. The residue, an oily liquid, was purified by vacuum distillation (125° C./2 mbar). Pure product (IIIa) was obtained as a light yellow oil (8.9 g, 44%). $^1$H-NMR (CDCl$_3$): δ=7.44 (dd, J=3.6 Hz, J=1.2 Hz, 1H), 7.35 (dd, J=5.2 Hz, J=1.2 Hz, 1H), 7.17 (d, J=5.4 Hz, 1H), 7.10 (dd, J=5.1 Hz, J=3.6 Hz, 1H), 7.02 (d, J=5.4 Hz, 1H). $^{13}$C-NMR (CDCl$_3$): δ=134.73, 132.71, 132.21, 127.71, 126.53, 124.82, 108.29.

Example 2

3-(2,2'-Bithiophene-3yl)pentan-3-ol (IIa)

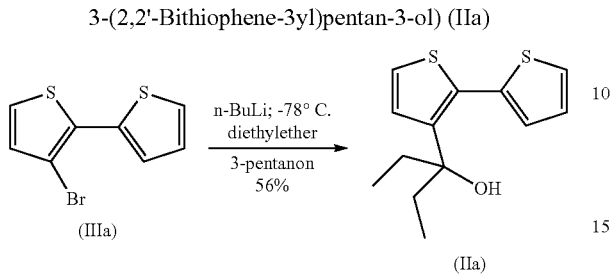

3-Bromo-2,2'-bithiophene (IIIa) (3.00 g, 12 mmol) in dry diethylether (100 mL) was added slowly to a solution of n-butyllithium (1.6 M in hexane, 7.50 mL, 12 mmol) in dry diethylether (100 mL) at −78° C. over 2 h under N$_2$. The mixture was stirred for 15 minutes at the same temperature. Freshly distilled 3-pentanone (1.29 mL, 12 mmol) was added via a syringe to the mixture at −78° C., followed by stirring overnight at room temperature. The reaction was quenched with an aqueous NH$_4$Cl-solution (2.5 M, 50 mL) and water (50 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIa) as a green oil (1.7 g, 56%). $^1$H-NMR (CDCl$_3$): δ=7.35 (dd, J=5.2 Hz, J=1.2 Hz, 1H), 7.24 (d, J=5.4 Hz, 1H), 7.10 (dd, J=3.6 Hz, J=1.2 Hz, 1H), 7.00 (dd, J=5.2 Hz, J=3.6 Hz, 1H), 6.95 (d, J=5.4 Hz, 1H), 1.75 (q, J=7.7 Hz, 4H), 0.80 (t, J=7.4 Hz, 6H). $^{13}$C-NMR (CDCl$_3$): δ=145.33, 136.11, 129.99, 129.76, 128.97, 127.87, 127.40, 125.54, 79.29, 35.79, 8.80.

Example 3

4,4-Diethyl-4H-cyclopenta[2,1-b:3,4-b']dithiophene (Ia)

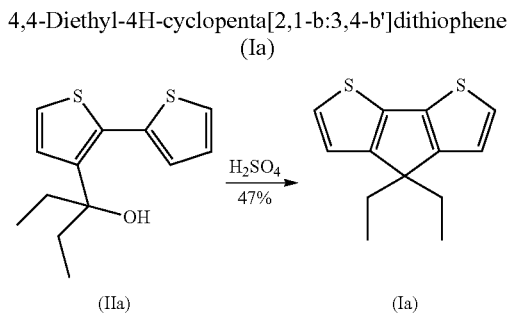

H$_2$SO$_4$ (7.0 mL) was added dropwise to 3-(2,2'-bithiophene-3-yl)pentan-3-ol (IIa) (2.67 g, 11 mmol) under stirring at room temperature. After stirring for 12 h, CH$_2$Cl$_2$ (100 mL) and water (100 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford pure dark yellow oil (Ia) (1.2 g, 47%). $^1$H-NMR (CDCl$_3$): δ=7.21 (d, J=4.8 Hz, 2H), 7.00 (d, J=4.8 Hz, 2H), 1.98 (q, J=6.8 Hz), 4H), 0.70 (t, J=7.0 Hz, 6H). $^{13}$C-NMR (CDCl$_3$): δ=157.89, 137.36, 125.09, 122.16, 54.76, 30.71, 9.74.

Example 4

4-(2,2'-Bithiophene-3-yl)-2,6-dimethylheptan-4-ol (IIb)

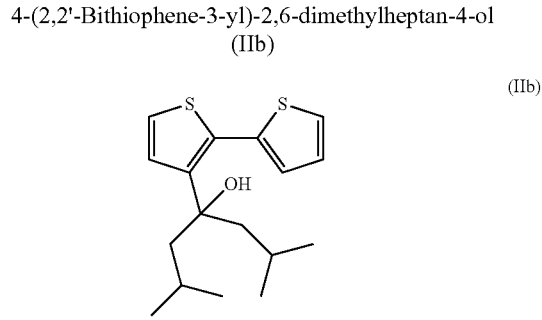

3-Bromo-2,2'-bithiophene (IIIa) (3.00 g, 12 mmol) in dry diethylether (100 mL) was added slowly to a solution of n-butyllithium (1.6 M in hexane, 7.50 mL, 12 mmol) in dry diethylether (100 mL) at −78° C. over 2 h under N$_2$. The mixture was stirred for 15 minutes at the same temperature. Freshly distilled 2,6-dimethyl-4-heptanone (2.17 mL, 12 mmol) was added via a syringe to the mixture at −78° C., followed by stirring overnight at room temperature. The reaction was quenched with an aqueous NH$_4$Cl-solution (2.5 M, 50 mL) and water (50 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIb) as a green oil (0.67 g, 18%). $^1$H-NMR (CDCl$_3$): δ=7.35 (dd, J=1.1 Hz, J=5.1 Hz, 1H), 7.22 (d, J=4.7 Hz, 1H), 7.08 (dd, J=1.1 Hz, J=3.6 Hz, 1H), 6.97 (d, J=4.7 Hz, 1H), 6.92 (dd, J=3.6 Hz, J=5.1 Hz, 1H), 1.85 (d, J=5.8 Hz, 4H), 1.08-0.78 (m, 2H), 0.50 (d, J=7.1 Hz, 12H). $^{13}$C-NMR (CDCl$_3$): δ=146.24, 136.18, 130.09, 129.31, 128.92, 127.85, 127.35, 125.48, 79.83, 53.28, 25.10, 24.93.

Example 5

4,4-Diisobutyl-4H-cyclopenta[1,2-b:5,4-b']dithiophene (Ib)

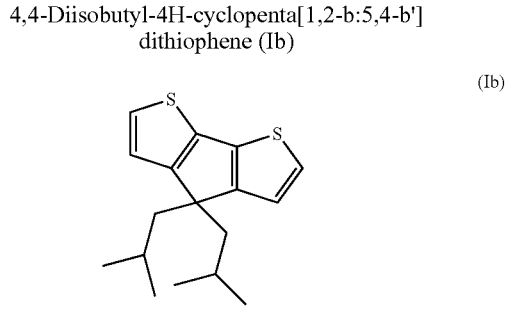

H$_2$SO$_4$ (1.45 mL) was added dropwise to 4-(2,2'-bithiophene-3-yl)-2,6-dimethylheptan-4-ol (IIb) (0.688 g, 2.23 mmol) under stirring at room temperature. After stirring for 12 h, CH$_2$Cl$_2$ (15 mL) and water (15 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Ib) (0.240 g, 35.0%). $^1$H-NMR (CDCl$_3$): δ=7.12 (d, J=4.8 Hz, 2H), 6.92 (d, J=4.8 Hz, 2H), 1.85 (d, J=5.8 Hz, 4H), 1.08-0.78 (m, 2H), 0.50 (d, J=7.1 Hz, 12H). $^{13}$C-NMR (CDCl$_3$): δ=158.45, 137.29, 124.99, 122.66, 53.69, 49.30, 25.46, 25.14.

Example 6

2-(2,2'-Bithiophene-3-yl)undecan-2-ol (IIc)

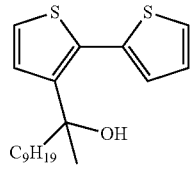

(IIc)

3-Bromo-2,2'-bithiophene (IIIa) (1.00 g, 4.08 mmol) in dry diethylether (35 mL) was added slowly to a solution of n-butyllithium (1.6 M in hexane, 2.50 mL, 4.0 mmol) in dry diethylether (35 mL) at −78° C. over 2 h under N$_2$. The mixture was stirred for 15 minutes at the same temperature. Freshly distilled 2-undecanone (0.84 mL, 4.08 mmol) was added via a syringe to the mixture at −78° C., followed by stirring overnight at room temperature. The reaction was quenched with an aqueous NH$_4$Cl-solution (2.5 M, 20 mL) and water (20 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIc) as a yellow oil (0.86 g, 64%). $^1$H-NMR (CDCl$_3$): δ=7.35 (dd, J=1.2 Hz, J=5.2 Hz, 1H), 7.22 (d, J=5.4 Hz, 1H), 7.12 (dd, J=1.2 Hz, J=3.5 Hz, 1H), 7.04 (d, J=5.4 Hz, 1H), 7.01 (dd, J=3.5 Hz, J=5.2 Hz, 1H), 1.49 (s, 3H), 1.38-1.15 (m, 16H), 0.96-0.80 (m, 3H). $^{13}$C-NMR (CDCl$_3$): δ=147.34, 136.12, 130.03, 129.50, 128.64, 127.76, 127.42, 125.40, 75.74, 44.52, 32.50, 30.99, 30.50, 30.29, 30.17, 29.94, 24.83, 23.32, 14.77.

Example 7

4-Nonyl-4-methyl-4H-cyclopenta[1,2-b:5,4-b']dithiophene (Ic)

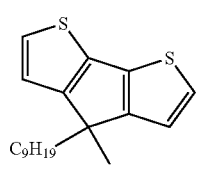

(Ic)

H$_2$SO$_4$ (1.33 mL) was added dropwise to 2-(2,2'-bithiophene-3-yl)undecan-2-ol (IIc) (0.70 g, 2.08 mmol) under stirring at room temperature. After stirring for 12 h, CH$_2$Cl$_2$ (15 mL) and water (15 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Ic) (0.106 g, 16.0%). $^1$H-NMR (CDCl$_3$): δ=7.13 (d, J=4.8 Hz, 2H), 6.94 (d, J=4.9 Hz, 2H), 1.82-1.75 (m, 2H), 1.41 (s, 3H), 1.29-1.07 (m, 14H), 0.84 (t, J=6.6 Hz, 3H). $^{13}$C-NMR (CDCl$_3$): δ=160.04, 136.50, 125.27, 121.95, 49.53, 39.66, 32.50, 30.63, 30.36, 30.20, 30.07, 29.91, 25.65, 24.36, 23.32, 14.77.

Example 8

6-([2,2'-Bithiophen]-3-yl)undecan-6-ol (IIu)

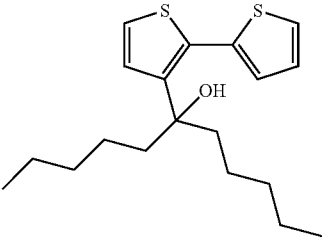

(IIu)

3-Bromo-2,2'-bithiophene (IIIa) (0.500 g, 2.04 mmol) in dry diethylether (20 mL) was added slowly to a solution of n-butyllithium (1.6 M in hexane, 1.25 mL, 2.04 mmol) in dry diethylether (20 mL) at −78° C. over 2 h under N$_2$. The mixture was stirred for 15 minutes at the same temperature. Freshly distilled 6-undecanone (0.42 mL, 2.04 mmol) was added via a syringe to the mixture at −78° C., followed by stirring overnight at room temperature. The reaction was quenched with an aqueous NH$_4$Cl-solution (2.5 M, 10 mL) and water (10 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIu) as a yellow oil (0.425 g, 62.0%). $^1$H-NMR (CDCl$_3$): δ=7.35 (dd, J=1.3 Hz, J=5.3 Hz, 1H), 7.23 (d, J=5.4 Hz, 1H), 7.09 (dd, J=1.3 Hz, J=3.5 Hz, 1H), 7.01 (dd, J=5.3, J=3.5 Hz, 1H), 6.98 (d, J=5.4 Hz, 1H), 2.02 (s, 1H), 1.83-1.60 (m, 4H), 1.42-1.05 (m, 12H), 0.84 (t, J=6.7 Hz, 6H). $^{13}$C-NMR (CDCl$_3$): δ=146.06, 136.07, 129.93, 129.19, 128.92, 127.78, 127.31, 125.41, 78.68, 43.60, 32.75, 24.00, 23.21, 14.70.

Example 9

4,4-Dipentyl-4H-cyclopenta[1,2-b:5,4-b']dithiophene (Iu)

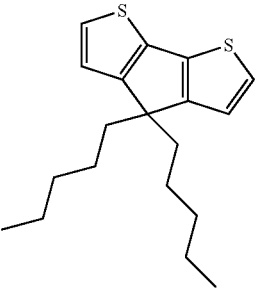

(Iu)

H$_2$SO$_4$ (0.61 mL) was added dropwise to 6-([2,2'-bithiophen]-3-yl)undecan-6-ol (IIu) (0.33 g, 0.98 mmol) under stirring at room temperature. After stirring for 12 h, CH$_2$Cl$_2$ (15 mL) and water (15 mL) were added. The organic layer was separated and the aqueous layer was extracted with CH$_2$Cl$_2$. The combined organic extracts were successively washed with saturated NaHCO$_3$ and brine. After drying over magnesium sulfate, the solvent was removed in vacuo. The crude oil was purified with column chromatography (eluent hexane) to afford a pure dark yellow oil (Iu) (0.0937 g, 30.0%). $^1$H-NMR (CDCl$_3$): δ=7.13 (d, J=4.8 Hz, 2H), 6.92 (d, J=4.9 Hz, 2H), 1.83-1.78 (m, 4H), 1.21-1.04 (m, 8H), 1.00-0.87 (m, 4H), 0.77 (t, J=6.3 Hz, 6H). $^{13}$C-NMR (CDCl$_3$): δ=158.76, 137.09, 125.09, 122.29, 53.87, 38.34, 32.87, 24.82, 23.05, 14.69

Example 10

[2,2'-Bithiophen]-3-yl(cyclohexyl)methanol

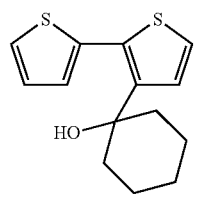

(IIk)

3-Bromo-2,2'-bithiophene (IIIa) (0.50 g, 2.04 mmol) in dry diethylether (20 mL) was added slowly to a solution of n-butyllithium (1.6 M in hexane, 1.25 mL, 2.04 mmol) in dry diethylether (20 mL) at −78° C. over 2 h under N$_2$. The mixture was stirred for 15 minutes at the same temperature. Freshly distilled cyclohexanone (0.21 mL, 2.04 mmol) was added via a syringe to the mixture at −78° C., followed by stirring overnight at room temperature. The reaction was quenched with an aqueous NH$_4$Cl-solution (2.5 M, 10 mL) and water (10 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIk) as a yellow oil (0.264 g, 49.0%). $^1$H-NMR (CDCl$_3$): δ=7.27 (dd, J=5.2 Hz, J=1.2 Hz, 1H), 7.14 (d, J=5.4 Hz, 1H), 7.14 (dd, J=3.8 Hz, J=1.2 Hz, 1H), 7.07 (d, J=5.4, 1H), 6.95 (dd, J=5.2 Hz, J=3.8 Hz 1H), 2.32 (br s, 1H), 1.84-1.72 (m, 4H), 1.69-1.51 (m, 4H), 1.50-1.39 (m, 2H).

Example 11

[2,2'-Bithiophen]-3-yldiphenylmethanol (IIj)

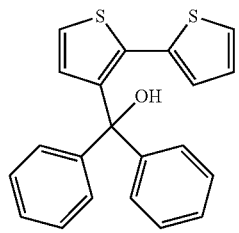

(IIj)

3-Bromo-2,2'-bithiophene (IIIa) (0.50 g, 2.04 mmol) in dry diethylether (20 mL) was added slowly to a solution of n-butyllithium (1.6 M in hexane, 1.25 mL, 2.04 mmol) in dry diethylether (20 mL) at −78° C. over 2 h under N$_2$. The mixture was stirred for 15 minutes at the same temperature. Benzophenone (0.33 g, 1.81 mmol) was added to the mixture at −78° C., followed by stirring overnight at room temperature. The reaction was quenched with an aqueous NH$_4$Cl-solution (2.5 M, 10 mL) and water (10 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by column chromatography (eluent hexane/EtOAc 90:10) to afford the title compound (IIj) as a yellow oil (0.202 g, 29.0%). $^1$H-NMR (CDCl$_3$): δ=7.35-7.26 (m, 10H), 7.23 (dd, J=5.1, J=1.2 Hz, 1H), 7.11 (d, J=5.4 Hz, 1H), 6.85 (dd, J=5.1, J=3.5 Hz, 1H), 6.66 (dd, J=3.5 Hz, J=1.2 Hz, 1H), 6.38 (d, J=5.4, 1H), 3.43 (br s, 1H).

Example 12

9-([2,2'-Bithiophen]-3-yl)heptadecan-9-ol (IIe)

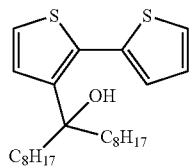

(IIe)

3-Bromo-2,2'-bithiophene (IIIa) (5.00 g, 20 mmol) in dry diethylether (170 mL) was added slowly to a solution of n-butyllithium (1.6 M in hexane, 12.5 mL, 20 mmol) in dry diethylether (170 mL) at −78° C. over 2 h under N$_2$. The mixture was stirred for 15 minutes at the same temperature. Heptadecan-9-one (6.22 g, 24 mmol) was added to the mixture at −78° C., followed by stirring overnight at room temperature. The reaction was quenched with an aqueous NH$_4$Cl-solution (2.5 M, 85 mL) and water (85 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by gradient column chromatography (eluent hexane/EtOAc 95:5) to afford the title compound (IIe) as a yellow oil (6.3 g, 75%). $^1$H-NMR (CDCl$_3$): δ=7.34 (dd, J=5.1 Hz, J=1.3 Hz, 1H), 7.22 (d, J=5.3 Hz, 1H), 7.07 (dd, J=3.5 Hz, J=1.2 Hz, 1H), 6.99 (dd, J=5.1, J=3.5 Hz, 1H), 6.97 (d, J=5.3 Hz, 1H), 2.36 (t, J=7.7 Hz, 4H), 1.39-1.07 (m, 20H), 0.91-0.81 (m, 6H).

Example 13a 4,4-Dioctyl-4H-cyclopenta[1,2-b:5,4-b']dithiophene (Ie)

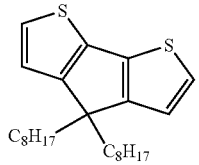

(Ie)

H$_2$SO$_4$ (9.38 mL) was added dropwise to 9-([2,2'-bithiophen]-3-yl)heptadecan-9-ol (IIe) (6.32 g, 15 mmol) under stirring at room temperature. After stirring for 12 h, CH$_2$Cl$_2$ (130 mL) and water (130 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Ie) (1.81 g, 30.0%). $^1$H-NMR (CDCl$_3$): δ=7.14 (d, J=4.8 Hz, 2H), 6.93 (d, J=5.1 Hz, 2H), 1.87-1.79 (m, 4H), 1.40-1.06 (m, 24H), 0.95-0.82 (m, 6H).

Example 13b 4,4-Dioctyl-4H-cyclopenta[1,2-b:5,4-b']dithiophene (Ie)

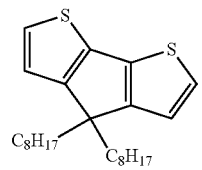

H$_2$SO$_4$ (9.38 mL) was added dropwise to 9-([2,2'-bithiophen]-3-yl)heptadecan-9-ol (IIe) (6.20 g, 15 mmol) in 200 ml n-octane under stirring at room temperature. After stirring for 12 h, CH$_2$Cl$_2$ (130 mL) and water (130 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Ie) (3.19 g, 52.9%). $^1$H-NMR (CDCl$_3$): δ=7.14 (d, J=4.8 Hz, 2H), 6.93 (d, J=5.1 Hz, 2H), 1.87-1.79 (m, 4H), 1.40-1.06 (m, 24H), 0.95-0.82 (m, 6H).

Example 14

7-([2,2'-Bithiophen]-3-yl)-5-ethylpentadecan-7-ol (IId)

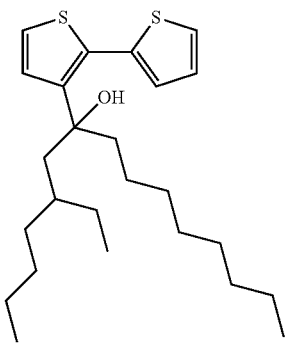

3-Bromo-2,2'-bithiophene (IIIa) (1.00 g, 3.94 mmol) in dry diethylether (35 mL) was added slowly to a solution of n-butyllithium (1.6 M in hexane, 2.41 mL, 3.86 mmol) in dry diethylether (35 mL) at −78° C. over 2 h under N$_2$. The mixture was stirred for 15 minutes at the same temperature. 5-ethylpentadecan-7-one (1.00 g, 3.94 mmol) was added to the mixture at −78° C., followed by stirring overnight at room temperature. The reaction was quenched with an aqueous NH$_4$Cl-solution (2.5 M, 20 mL) and water (20 mL) at 0° C. The organic phase was separated and the aqueous phase was extracted with diethylether. The combined organic phases were washed with brine, dried over MgSO$_4$ and evaporated under reduced pressure to give a crude oil. The oily residue was purified by gradient column chromatography (eluent hexane/EtOAc 95:5) to afford the title compound (11d) as a yellow oil (0.583 g, 36.0%). $^1$H-NMR (CDCl$_3$): δ=7.35 (dd, J=5.2 Hz, J=1.2 Hz, 1H), 7.22 (d, J=5.4 Hz, 1H), 7.08 (dd, J=3.5 Hz, J=1.2 Hz, 1H), 7.00 (dd, J=5.2, J=3.5 Hz, 1H), 6.95 (d, J=5.4 Hz, 1H), 1.91 (d, J=2.5 Hz, 2H), 1.83-1.56 (m, 3H), 1.42-1.00 (m, 20H), 0.88-0.65 (m, 9H).

Example 15a 4-(2-Ethylhexyl)-4-octyl-4H-cyclopenta[1,2-b:5,4-b']dithiophene (Id)

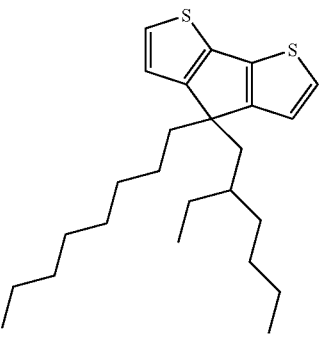

H$_2$SO$_4$ (0.37 mL) was added dropwise to 7-([2,2'-bithiophen]-3-yl)-5-ethylpentadecan-7-ol (IId) (0.25 g, 0.60 mmol) under stirring at room temperature. After stirring for 12 h, CH$_2$Cl$_2$ (15 mL) and water (15 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Id) (0.040 g, 17%). $^1$H-NMR (CDCl$_3$): δ=7.12 (d, J=4.8 Hz, 2H), 6.93 (d, J=4.8 Hz, 2H), 1.90 (t, 2H), 1.82 (m, 2H), 1.28-1.12 (m, 5H), 1.00-0.74 (m, 16H), 0.62 (t, 9H).

Example 15b 4-(2-Ethylhexyl)-4-octyl-4H-cyclopenta[1,2-b:5,4-b']dithiophene (Id)

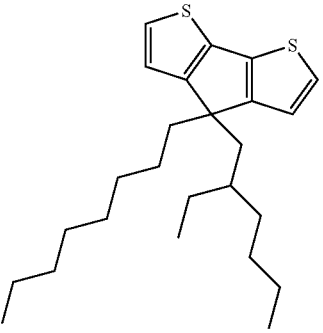

H$_2$SO$_4$ (0.37 mL) was added dropwise to 7-([2,2'-bithiophen]-3-yl)-5-ethylpentadecan-7-ol (IId) (1.59 g, 3.79 mmol) in 50 ml n-octane under stirring at room temperature. After stirring for 12 h, CH$_2$Cl$_2$ (15 mL) and water (15 mL) were added. The organic layer was separated and the aqueous layer was extracted with CH$_2$Cl$_2$. The combined organic extracts were successively washed with saturated NaHCO$_3$ and brine. After drying over MgSO$_4$, the solvent was removed in vacuo. The crude oil was purified with column chromatography (eluent hexane) to afford a pure dark yellow oil (Id) (0.852 g, 57%). ¹H-NMR (CDCl₃): δ=7.12 (d, J=4.8 Hz, 2H), 6.93 (d, J=4.8 Hz, 2H), 1.90 (t, 2H), 1.82 (m, 2H), 1.28-1.12 (m, 5H), 1.00-0.74 (m, 16H), 0.62 (t, 9H).

Examples 16 and 17 Follow the Following Scheme

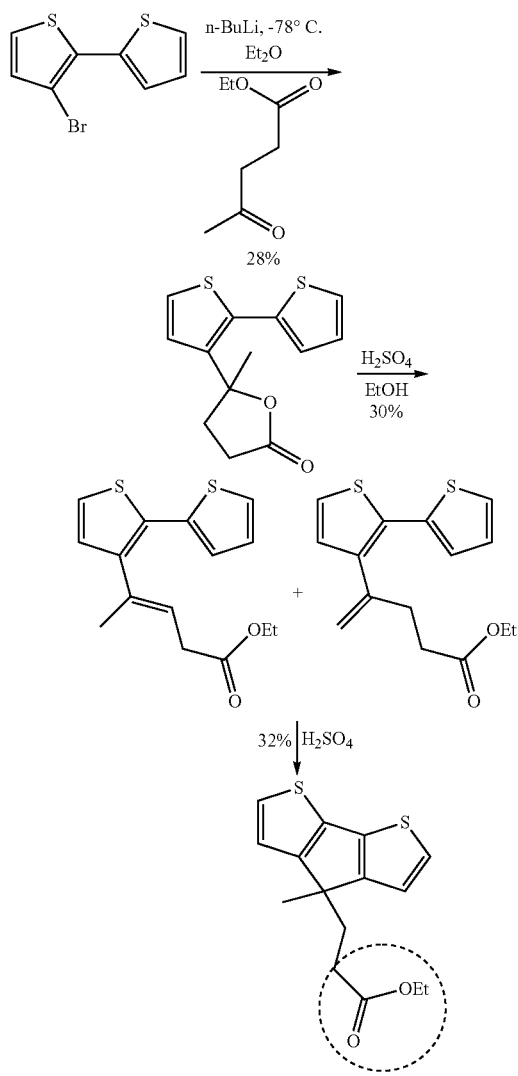

Example 16

5-([2,2'-Bithiophen]-3-yl)-5-methyldihydrofuran-2(3H)-one

3-Bromo-2,2'-bithiophene (1.00 g, 4.08 mmol) in dry diethylether (35 mL) was added slowly to a solution of n-butyllithium (1.6 M in hexane, 2.50 mL, 4.08 mmol) in dry diethylether (35 mL) at −78° C. over 2 h under N₂. The mixture was stirred for 15 minutes at the same temperature. Freshly distilled ethyllevulinate (0.58 mL, 4.08 mmol) was added to the mixture at −78° C., followed by stirring overnight at room temperature. The reaction was quenched with an aqueous NH₄Cl-solution (2.5 M, 20 mL) and water (80 mL) at 0° C. The organic phase was separated and the aqueous phase was extracted with diethylether. The combined organic phases were washed with brine, dried over MgSO₄ and evaporated under reduced pressure to give a crude oil. The oily residue was purified by gradient column chromatography (eluent hexane/EtOAc 95:5) to afford the title compound as a yellow oil (0.35 g, 28%). ¹H-NMR (CDCl₃): δ=7.38 (dd, J=5.1 Hz, J=1.3 Hz, 1H), 7.27 (d, J=5.3 Hz, 1H), 7.15 (d, J=5.3 Hz, 1H), 7.09 (dd, J=3.7 Hz, J=1.3 Hz, 1H), 7.04 (dd, J=5.1 Hz, J=3.7 Hz, 1H), 2.59-2.40 (m, 2H), 2.19-2.12 (m, 2H), 1.69 (s, 3H).

Example 17

Ethyl 3-(4-methyl-4H-cyclopenta[1,2-b:5,4-b']dithiophen-4-yl)propanoate. (IIv)

(IIv)

H₂SO₄ (0.30 mL) was added dropwise to a solution of 5-([2,2'-bithiophen]-3-yl)-5-methyldihydrofuran-2(3H)-one (0.030 g, 0.11 mmol) in ethanol (2 mL) under stirring at room temperature. After stirring for 12 h, CH₂Cl₂ (15 mL) and water (15 mL) were added. The organic layer was separated and the aqueous layer was extracted with CH₂Cl₂. The combined organic extracts were successively washed with saturated NaHCO₃ and brine. After drying over MgSO₄, the solvent was removed in vacuo. The crude oil was purified with column chromatography (eluent dichloromethane) to afford a pure dark yellow oil (IIv) (0.0106 g, 31.9%). ¹H-NMR (CDCl₃): δ=7.15 (d, J=4.9 Hz, 2H), 6.93 (d, J=4.7 Hz, 2H), 3.96 (q, J=7.1 Hz, 2H), 2.28-2.21 (m, 2H), 1.80-1.74 (m, 2H), 1.45 (s, 3H), 1.13 (t, J=7.2 Hz, 3H).

Example 18

3-Ethylheptanenitrile (VI)

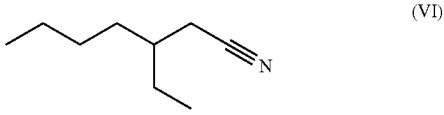

(VI)

A solution of KCN (3.8 g, 58 mmol) was stirred in DMF (150 mL) at room temperature. After the mixture was stirred for 2 h, a solution of 2-ethylhexylbromide (10 g, 52 mmol) in DMF (250 mL) was added dropwise at the same temperature. After stirring for 12 h at room temperature, the reaction mixture was concentrated by evaporation in vacuo. The crude product was diluted with water (100 mL) and diethyl ether (100 mL). The organic layer was separated and the aqueous layer was extracted with diethyl ether. The combined organic layers were subsequently washed with NaOH-solution (2.5 M), saturated bicarbonate solution and brine, dried over MgSO$_4$ and concentrated by evaporation in vacuo. The resulting brown oil was purified by vacuum distillation (45° C., $10^{-2}$ mbar) to afford a clearly yellow oil (VI). (3.2 g, 44%). $^1$H-NMR (CDCl$_3$): δ=2.82-2.69 (m, 2H), 2.22-2.15 (m, 1H), 1.55-1.00 (m, 11H), 0.83-0.68 (m, 3H)

Example 19

5,9-Diethyltridecan-7-one (VII)

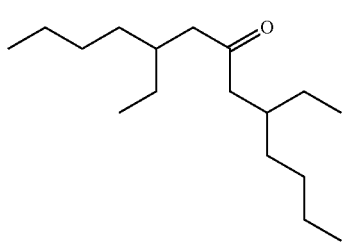

(VII)

A Grignard solution of 2-ethylhexylmagnesiumbromide in diethylether (1.0 M, 47 mL, 47 mmol) was slowly added via syringe to a stirred mixture of 3-ethylheptanenitrile (VI) (3.3 g, 24 mmol) in diethyl ether (50 mL) at 0° C. under N$_2$ atmosphere. After stirring for 12 h at reflux temperature, the reaction was quenched with an aqueous HCl-solution (2.0 M, 50 mL) at 0° C. and subsequently vigorously stirred for an additional 3 h at room temperature. The organic phase was separated and the aqueous phase was extracted with diethylether. The combined organic phases were washed with a saturated bicarbonate solution and brine, dried over MgSO$_4$ and evaporated under reduced pressure to give a crude brown oil. The resulting brown oil was purified by vacuum distillation (95° C., $10^{-2}$ mbar) to afford a yellow oil (VII). (5.8 g, 35%). $^1$H-NMR (CDCl$_3$): δ=2.66-2.63 (m, 2H), 2.24 (d, J=6.9 Hz, 4H), 1.36-1.04 (m, 16H), 0.91-0.63 (m, 12H). $^{13}$C-NMR (CDCl$_3$): δ=211.59, 48.32, 39.74, 35.53, 33.57, 30.22, 26.65, 23.59, 14.61.

Example 20

Heptadecan-9-one (VIII)

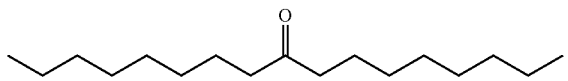

(VIII)

A Grignard solution of n-octylmagnesiumbromide in diethylether (2.0 M, 100 mL, 0.2 mol) was slowly added via syringe to a stirred mixture of n-octylcyanide (13.92 g, 0.1 mol) in diethyl ether (100 mL) at 0° C. under N$_2$ atmosphere. After stirring for 12 h at reflux temperature, the reaction was quenched with an aqueous HCl-solution (2.0 M, 50 mL) at 0° C. and subsequently vigorously stirred for an additional 3 h at room temperature. The organic phase was separated and the aqueous phase was extracted with diethylether. The combined organic phases were washed with a saturated bicarbonate solution and brine, dried over MgSO$_4$ and evaporated under reduced pressure to give an orange solid. The resulting solid was purified recrystallization from methanol to afford yellow crystals (VIII) (18.06 g, 71%). $^1$H-NMR (CDCl$_3$): δ=2.33 (t, J=7.4 Hz, 4H), 1.58-1.44 (m, 4H), 1.30-1.10 (s, 20H), 0.82 (t, J=6.4 Hz, 6H). $^{13}$C-NMR (CDCl$_3$): δ=212.33, 43.42, 32.44, 30.01, 29.90, 29.78, 24.49, 23.26, 14.70.

Example 21

5-Ethylpentadecan-7-one (IX)

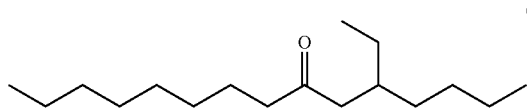

(IX)

A Grignard solution of 2-ethylhexylmagnesiumbromide in diethylether (1.0 M, 110 mL, 0.11 mol) was slowly added via syringe to a stirred mixture of n-octylcyanide (4.66 g, 55 mmol) in diethyl ether (100 mL) at 0° C. under N$_2$ atmosphere. After stirring for 12 h at reflux temperature, the reaction was quenched with an aqueous HCl-solution (2.0 M, 50 mL) at 0° C. and subsequently vigorously stirred for an additional 3 h at room temperature. The organic phase was separated and the aqueous phase was extracted with diethylether. The combined organic phases were washed with a saturated bicarbonate solution and brine, dried over MgSO$_4$ and evaporated under reduced pressure to give a yellow solid. The resulting solid was purified by recrystallization from acetone to afford white crystals (IX) (4.51 g, 32%). $^1$H-NMR (CDCl$_3$): δ=2.99-2.79 (m, 4H), 2.64-2.50 (m, 1H), 1.82-1.55 (m, 4H), 1.57-1.03 (m, 18H), 0.89-0.71 (m, 9H). $^{13}$C-NMR (CDCl$_3$): δ=164.35, 34.89, 32.44, 30.31, 30.09, 29.90, 29.79, 28.48, 28.31, 25.71, 23.26, 14.71.

Example 22

2,6-Dibromo-4,4-dioctyl-4H-cyclopenta[1,2-b:5,4-b']dithiophene

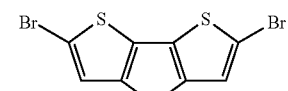

(XIVe)

Protected from light, a solution of NBS (1.13 g, 6.37 mmol) in DMF (40 mL) was added dropwise to a solution of 4,4-dioctyl-4H-cyclopenta[1,2-b:5,4-b']dithiophene (Ie) (0.80 g, 2.0 mmol) in DMF (40 mL), after which the mixture was stirred for 48 h. Subsequently the reaction was quenched with an aqueous NaOH-solution (2.5 M, 50 mL) at 0° C. and subsequently extracted with diethyl ether. The combined organic layers were washed with saturated bicarbonate solution and brine, dried over MgSO$_4$ and concentrated by evaporation in vacuo. The crude green oil was purified by column chromatography using silica gel (eluent hexane). The compound XIVe was obtained as a lightly yellow oil. (0.40 g, 50%). $^1$H-NMR (CDCl$_3$): δ=6.91 (s, 2H), 1.83-1.68 (m, 4H), 1.40-1.02 (m, 24H), 0.98-0.75 (m, 6H).

Example 23

Undec-10-enoyl chloride (X)

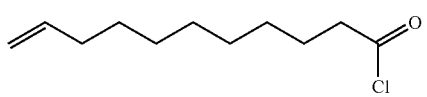

A mixture of toluene (12 mL) and SOCl$_2$ (7.75 g, 65 mmol) and undec-10-enoic acid (1.00 g, 5.43 mmol) were refluxed for 1.5 h. The solvent and remaining SOCl$_2$ were distilled off and the product (X) was further used in the thioester synthesis. $^1$H-NMR (CDCl$_3$): δ=5.90-5.74 (m, 1H), 5.06-4.91 (m, 2H), 2.87 (t, J=7.2 Hz, 2H), 2.06 (q, J=13.7 Hz, J=6.7 Hz, 2H), 1.78-1.61 (m, 2H), 1.49-1.23 (m, 8H).

Example 24

Pyridin-2-yl undec-10-enethioate (XI)

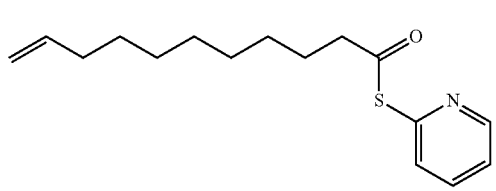

A solution of triethylamine (2.5 mL), THF (20 mL) and 2-mercaptopyridine (0.77 g, 6.95 mmol) was stirred for 15 minutes at 0° C. A solution of undec-10-enoyl chloride (X) (1.17 g, 5.79 mmol) in THF (20 mL) was added all at once. Immediately the reaction was then quenched by adding an aqueous HCl-solution (2.0 M, 50 mL) at 0° C. and subsequently extracted with diethyl ether. The organic phase was separated and the aqueous phase was extracted with diethylether. The combined organic phases were washed with a saturated bicarbonate solution and brine, dried over MgSO$_4$ and evaporated under reduced pressure to give a yellow oil. The crude green oil was purified by column chromatography using silica gel (eluent CH$_2$Cl$_2$). The compound (XI) was obtained as a lightly yellow oil. (0.64 g, 40%). $^1$H-NMR (CDCl$_3$): δ=8.60-8.55 (m, 1H), 7.73-7.65 (m, 1H), 7.60-7.54 (m, 1H), 7.27-7.20 (m, 1H), 5.84-5.68 (m, 1H), 5.01-4.84 (m, 2H), 2.65 (t, J=7.5 Hz, 2H), 1.99 (q, J=13.7 Hz, J=6.7 Hz, 2H), 1.73-1.61 (m, 2H), 1.40-1.17 (m; 10H).

Example 25

5-Ethylheptadec-16-en-7-one (XII)

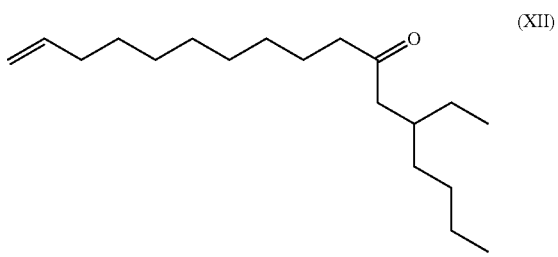

A Grignard solution of 2-ethylhexylmagnesium-bromide in diethylether (1.0 M, 1.96 mL, 1.96 mmol) was slowly added via syringe to a stirred mixture of pyridin-2-yl undec-10-enethioate (0.54 g, 1.96 mmol) in THF (50 mL) at 0° C. under N$_2$ atmosphere. After vigorously stirring for another 30 minutes, the reaction was completed by adding (2.0 M, 50 mL). The organic phase was separated and the aqueous phase was extracted with diethylether. The combined organic phases were washed with a saturated bicarbonate solution and brine, dried over MgSO$_4$ and evaporated under reduced pressure to give a yellow oil. The resulting oil was purified by vacuum distillation at 90-100° C. at 10$^{-2}$ mbar. $^1$H-NMR (CDCl$_3$): δ=5.85-5.67 (m, 1H), 5.00-4.83 (m, 2H), 2.37-2.22 (m, 4H), 1.99 (q, J=14.0 Hz, J=6.9 Hz, 2H), 1.89-1.76 (m, 1H), 1.61-1.44 (m; 4H), 1.39-1.09 (m, 16H), 0.90-0.74 (m, 6H).

Example 26

Acid Tests Toward Ring Closure of Compound IIa to Obtain the Cyclopentadithiophene Ia The table below summarizes the results of ring closure reactions performed on compound IIa with various protic acids. The tests were performed at room temperature for 12 h.

TABLE 4

| Acid | pKa | Ring closure |
|---|---|---|
| HCl | −8.00 | No |
| HNO$_3$ | −1.4 | No |
| H$_2$SO$_4$ | −3 | Yes |
| H$_2$CrO$_4$ | −0.98 | Yes |
| H$_3$PO$_4$ | 2.12 | No |
| p-TsOH | −2.8 | No |

From this table, it is apparent that only diprotic acids having a negative pKa permits to perform the ring closure reaction. It is surprising to note that monoprotic acids do not work even when their pKa is low.

It is to be understood that although preferred embodiments, specific constructions and configurations, as well as materials, have been discussed herein for devices according to the present preferred embodiments, various changes or modifications in form and detail may be made without departing from the scope and spirit of this preferred embodiments. For example, any formulas given above are merely representative of procedures that may be used. Functionality may be added or deleted from the block diagrams and operations may be interchanged among functional blocks. Steps may be added or deleted to methods described within the scope of the present preferred embodiments.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for synthesizing a compound having a general formula (I):

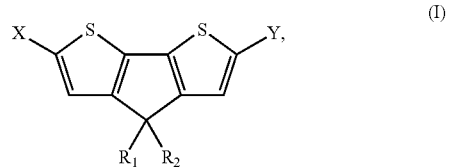

the method comprising:
contacting a compound having a general formula (II):

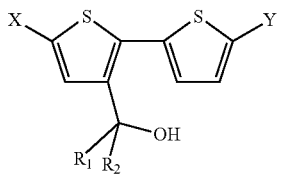
(II)

with a diprotic acid having a negative pKa, wherein $R_1$ and $R_2$ are independently selected from the group consisting of $C_{1-20}$ alkyl, halo $C_{1-20}$ alkyl, $C_{4-10}$ cycloalkyl, $C_{1-3}$ alkyl $C_{1-10}$ alkanoate, $C_{1-3}$ alkyl $C_{1-10}$ alkanamide, $C_{2-10}$ alkenyl, $C_{3-10}$ cycloalkenyl, aryl $C_{1-5}$ alkyl, di-aryl $C_{1-5}$ alkyl, tri-$C_{1-20}$ aryl $C_{1-5}$ alkyl, aryl $C_{2-5}$ alkenyl, $C_{2-10}$ alkynyl, $C_{1-10}$ alkanol, $C_{1-10}$ alkanethiol, aryl, heterocyclic radical, heteroaryl, $C_{1-3}$ alkoxy $C_{1-3}$ alkyl, di-$C_{1-3}$ alkoxy $C_{1-3}$ alkyl, $C_{1-3}$ alkyloxy aryl $C_{1-3}$ alkyl, $C_{1-3}$ alkyl aryl, $C_{1-3}$ alkyl sulfanyl $C_{1-3}$ alkyl, $C_{1-3}$ alkyl aryl sulfanyl $C_{1-3}$ alkyl, aryloxy $C_{1-3}$ alkyl, N,N—$C_{1-3}$ dialkyl $C_{1-3}$ alkylamine, N—$C_{1-3}$ alkyl $C_{1-3}$ alkylamine, and aryl sulphonyl $C_{1-3}$ alkyl, or $R_1$ and $R_2$ together form a cycloalkyl group or a heterocyclic group, and wherein X and Y are independently selected from the group consisting of hydrogen, chloro, bromo, iodo, boronic acid, boronate esters, borane, pseudohalogen, and organotin.

2. The method according to claim 1, wherein $R_1$ and $R_2$ are different.

3. The method according to claim 1, wherein the diprotic acid is present in an amount of from 2 to 15 equivalents related to compound (II).

4. The method according to claim 1, wherein the acid has a pKa maximum of −0.5.

5. The method according to claim 1, wherein the acid is $H_2SO_4$ or $H_2CrO_4$.

6. The method according to claim 1, further comprising preparing a compound of general formula (II) by reacting a compound having a general formula (III):

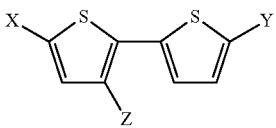
(III)

with a base, then with a compound having a general formula $R_1(CO)R_2$, wherein Z is a halogen or a pseudohalogen and wherein X and Y are independently selected from the group consisting of hydrogen, chloro, bromo, iodo, boronic acid, boronate ester, borane, pseudohalogen and organotin.

7. The method of claim 6, wherein the base is a strong base.

8. The method of claim 7, wherein the base is an alkyl lithium.

9. The method of claim 8, wherein the alkyl lithium is n-butyllithium.

10. The method according to claim 6, wherein the halogen is a bromine atom.

11. A chemical compound of a general formula (I):

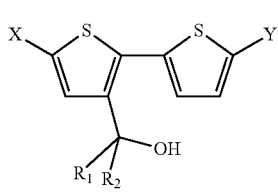
(II)

wherein $R_1$ and $R_2$ are independently selected from the group consisting of $C_{1-20}$ alkyl, halo $C_{1-20}$ alkyl, $C_{4-10}$ cycloalkyl, $C_{1-3}$ alkyl $C_{1-10}$ alkanoate, $C_{1-3}$ alkyl $C_{1-10}$ alkanamide, $C_{2-10}$ alkenyl, $C_{3-10}$ cycloalkenyl, aryl $C_{1-5}$ alkyl, di-aryl $C_{1-5}$ alkyl, tri-$C_{1-20}$ aryl $C_{1-5}$ alkyl, aryl $C_{2-5}$ alkenyl, $C_{2-10}$ alkynyl, $C_{1-10}$ alkanol, $C_{1-10}$ alkanethiol, aryl, heterocyclic radical, heteroaryl, $C_{1-3}$ alkoxy $C_{1-3}$ alkyl, di-$C_{1-3}$ alkoxy $C_{1-3}$ alkyl, $C_{1-3}$ alkyloxy aryl $C_{1-3}$ alkyl, $C_{1-3}$ alkyl aryl, $C_{1-3}$ alkyl sulfanyl $C_{1-3}$ alkyl, $C_{1-3}$ alkyl aryl sulfanyl $C_{1-3}$ alkyl, aryloxy $C_{1-3}$ alkyl, N,N—$C_{1-3}$ dialkyl $C_{1-3}$ alkylamine, N—$C_{1-3}$ alkyl $C_{1-3}$ alkylamine, and aryl sulphonyl $C_{1-3}$ alkyl, or $R_1$ and $R_2$ together form a cycloalkyl group or a heterocyclic group, and wherein X and Y are independently selected from the group consisting of hydrogen, chloro, bromo, iodo, boronic acid, boronate ester, borane, pseudohalogen and organotin.

\* \* \* \* \*

UNITED STATES PATENT AND TRADEMARK OFFICE
CERTIFICATE OF CORRECTION

PATENT NO. : 8,329,923 B2  Page 1 of 1
APPLICATION NO. : 13/028539
DATED : December 11, 2012
INVENTOR(S) : Vanderzande et al.

It is certified that error appears in the above-identified patent and that said Letters Patent is hereby corrected as shown below:

| Column | Line | |
|---|---|---|
| In the Specifications: | | |
| 2 | 65 | Change "$C_{1-10}$alkanethiol," to --$C_{1-10}$ alkanethiol,--. |
| 3 | 25 | Change "$C_{1-10}$alkanethiol," to --$C_{1-10}$ alkanethiol,--. |
| 69 | 67 | Change "(11d)" to --(IId)--. |
| In the Claims: | | |
| 80 | 35 | In Claim 11, change "$C_{1-10}$alkanethiol," to --$C_{1-10}$ alkanethiol,--. |

Signed and Sealed this
Eighteenth Day of June, 2013

Teresa Stanek Rea
*Acting Director of the United States Patent and Trademark Office*